(12) United States Patent
Singh et al.

(10) Patent No.: US 8,278,057 B2
(45) Date of Patent: Oct. 2, 2012

(54) ADDRESSABLE ANTIBODY ARRAYS AND METHODS OF USE

(75) Inventors: Sharat Singh, Rancho Santa Fe, CA (US); Shui Long Wang, San Diego, CA (US)

(73) Assignee: Nestec S.A., Vevey (CH)

( * ) Notice: Subject to any disclaimer, the term of this patent is extended or adjusted under 35 U.S.C. 154(b) by 498 days.

(21) Appl. No.: 12/500,553

(22) Filed: Jul. 9, 2009

(65) Prior Publication Data

US 2010/0022408 A1    Jan. 28, 2010

Related U.S. Application Data

(63) Continuation of application No. PCT/US2009/037566, filed on Mar. 18, 2009, which is a continuation-in-part of application No. 12/209,863, filed on Sep. 12, 2008, now abandoned.

(60) Provisional application No. 60/972,724, filed on Sep. 14, 2007.

(51) Int. Cl.
*G01N 33/53* (2006.01)

(52) U.S. Cl. ........................................... 435/7.1

(58) Field of Classification Search .................. None
See application file for complete search history.

(56) References Cited

U.S. PATENT DOCUMENTS

| | | | | |
|---|---|---|---|---|
| 5,981,181 A | * | 11/1999 | Frommer et al. | 435/6.16 |
| 6,214,560 B1 | * | 4/2001 | Yguerabide et al. | 506/3 |
| 6,465,430 B1 | * | 10/2002 | Dower et al. | 514/7.8 |
| 6,503,759 B1 | | 1/2003 | Still et al. | |
| 2007/0065948 A1 | | 3/2007 | Menchen et al. | |
| 2007/0251824 A1 | | 11/2007 | Patton et al. | |
| 2009/0017560 A1 | | 1/2009 | Adamczyk et al. | |
| 2009/0023144 A1 | | 1/2009 | Sun | |
| 2009/0068110 A1 | | 3/2009 | Shang et al. | |
| 2009/0088332 A1 | * | 4/2009 | Ju et al. | 506/9 |
| 2010/0256006 A1 | * | 10/2010 | Kodadek | 506/9 |

* cited by examiner

*Primary Examiner* — Ann Lam
(74) *Attorney, Agent, or Firm* — Kilpatrick Townsend & Stockton LLP

(57) ABSTRACT

Systems and assay methods are disclosed for detecting an autoantibody in a sample. In certain instances, the systems and methods employ a mass tag releasably connected to an antigen. The tag is thereafter released for detection. A tag can be detected by mass spectrometry or in certain instances the tag is fluorescent. Methods for diagnosing a disease or disorder in a subject are also disclosed.

19 Claims, 16 Drawing Sheets

ADDRESSABLE ANTIBODY ARRAYS AND METHODS OF USE

CROSS-REFERENCES TO RELATED APPLICATIONS

This application is a continuation application of PCT/US2009/037566, filed Mar. 18, 2009, which application is a continuation-in-part of U.S. application Ser. No. 12/209,863, filed Sep. 12, 2008, which application claims the benefit of priority of U.S. Provisional Application No. 60/972,724, filed Sep. 14, 2007, the teachings of which are incorporated herein by reference in their entirety for all purposes.

BACKGROUND OF THE INVENTION

Detection of various autoantibodies in body fluids is a major part of the diagnosis of autoimmune diseases and the detection of cancer. Current methods used in clinical laboratories lack universal standards and include diverse techniques such as immunofluorescence microscopy, Western blotting, and ELISA, the results of which are not usually comparable. In addition, such techniques require measurement of each autoantibody separately, and thus are not practical for parallel, high-throughput analysis of multiple auto antibodies.

Antibodies that are reactive against self-antigens are characteristic of many autoimmune diseases, allergy, and cancer. Self-antigens include a diverse group of cell surface, cytoplasmic, and nuclear antigens with post-translational modifications.

U.S. Pat. No. 4,020,151 to Bolz et al. discloses methods for determining antigen/antibody concentration using sample antibody/antigen immobilized on a solid support. For example, sample antibody is immobilized on the support and then excess labeled antigen is followed. Unreactive labeled antigen is washed and the immunological complex is then measured.

U.S. Pat. No. 4,184,849 to Cambiaso et al. discloses a competitive assay for measuring antigens and antibodies. The presence of antibodies (Ab) and antigens (Ag) in a liquid is detected by mixing the liquid with two different reagents which mutually agglutinate, but whose agglutination is inhibited by the particular Ab or Ag in the assay. By detecting the extent of agglutination, the presence or absence of the Ab or Ag can be confirmed.

U.S. Patent Publication No. US 2006/166268 to Grus et al. discloses diagnosing glaucoma or assessing an individual's risk for developing glaucoma, wherein autoantibodies against ocular antigens are detected and measured in body fluids of an individual, and the autoantibody pattern is correlated with corresponding patterns of healthy individuals and glaucoma patients. The autoantibody pattern consists of at least 10-30 autoantibodies. The autoantibodies are detected and measured in a Western blot assay, chemiluminescence assay, ELISA, or RIA. The autoantibodies may also be detected and measured on a protein chip array using surface-enhanced laser desorption/ionization (SELDI) or matrix assisted laser desorption/ionization mass spectrometry techniques, preferably SELDI mass spectrometry technique.

The parallel detection of an addressable microarray system may be particularly useful in combination with mathematical tools by minimizing the matrix effects that exist between individual assays, such as in ELISAs, because the calibrators and the autoantibodies are analyzed under the same conditions; it therefore will generate comparable results for the measurement of multiple analytes.

In view of the foregoing, there exists a need for addressable microarrays combined with, for example, artificial intelligence analysis, which can provide additional improvements in high throughput, cost-effectiveness, and accuracy for molecular diagnosis of autoimmune diseases and cancer. The present invention satisfies these and other needs.

BRIEF SUMMARY OF THE INVENTION

The present invention provides systems and assay methods having advantages over traditional ELISA methods, but which retain the sensitivity of ELISA or RIP (Radio Immuno-Precipitation assay). The methods provided herein possess the ability to multiplex, minimize the amount of biological sample, and have enhanced sensitivity and specificity.

As such, the present invention provides an assay method for detecting an autoantibody comprising: contacting a tagged antigen with a sample having an autoantibody specific for the tagged antigen to form, or wherein the tagged antigen is transformed into, an immunological pair; contacting the immunological pair with a solid support having a binding member specific for the immunological pair to form, or wherein the immunological pair is transform into, a protein complex; separating the protein complex from the sample to form an isolated protein complex; and releasing the tag from the isolated protein complex for detection. The detection is preferably by mass spectrometric techniques.

In another embodiment, the present invention provides a method for diagnosing a disease or disorder in a subject, comprising: contacting a tagged antigen with a sample from the subject having an autoantibody specific for the tagged antigen to form, or wherein the tagged antigen is transform into, an immunological pair; contacting the immunological pair with a solid support having a binding member specific for the immunological pair to form, or wherein the immunological pair is transformed into, a protein complex; separating the protein complex from the sample to form an isolated protein complex; releasing the tag from the isolated protein complex for detection; and detecting the amount of the tag, wherein the amount of the tag is indicative of the amount of the autoantibody, and wherein the disease or disorder is determined to be present when the amount of the autoantibody differs from a control value representing the amount of the autoantibody in a sample from a subject not having the disease or disorder.

In yet another embodiment, the present invention provides an assay method for detecting an autoantibody in a sample from a subject, comprising: contacting a tagged antigen with a sample having an autoantibody specific for the tagged antigen to form, or wherein the tagged antigen is transformed into, an immunological pair; contacting the immunological pair with a solid support having a binding member specific for the immunological pair to form, or wherein the immunological pair is transformed into a protein complex; releasing the protein complex to form an isolated protein complex; and recapturing the isolated protein complex.

These and other objects and advantages will become more apparent when read with the accompanying detailed description and drawings that follow.

DETAILED DESCRIPTION OF THE INVENTION

I. General

In certain instances, the present invention provides assay methods and systems for the detection of autoantibodies. The methods and systems of the present invention provide advantages over traditional ELISA or RIP (Radio Immuno-Precipitation assay). In certain aspects, the present methods employ mass tags which are cleavable from the antigen, antigen support or conjugate. Such cleavability allows the tags to be distinguished on more than one basis; in particular, they can be separated (e.g., on the basis of chromatographic retention time) and then analyzed (e.g., a second basis is a spectral property such as mass spectroscopy or electrophoricity). Cleavability further allows tags to be detected at very low concentration levels because they can be removed from the matrix, the presence of which could provide spurious background signals. Cleavable tags are also amenable to rapid analysis by automated sampling systems, and allow for selective derivatization for detection via functional groups, eliminating any incompatibility between the mass tag and the reaction conditions used in the assay.

II. Assay Methods

Figure 1A:
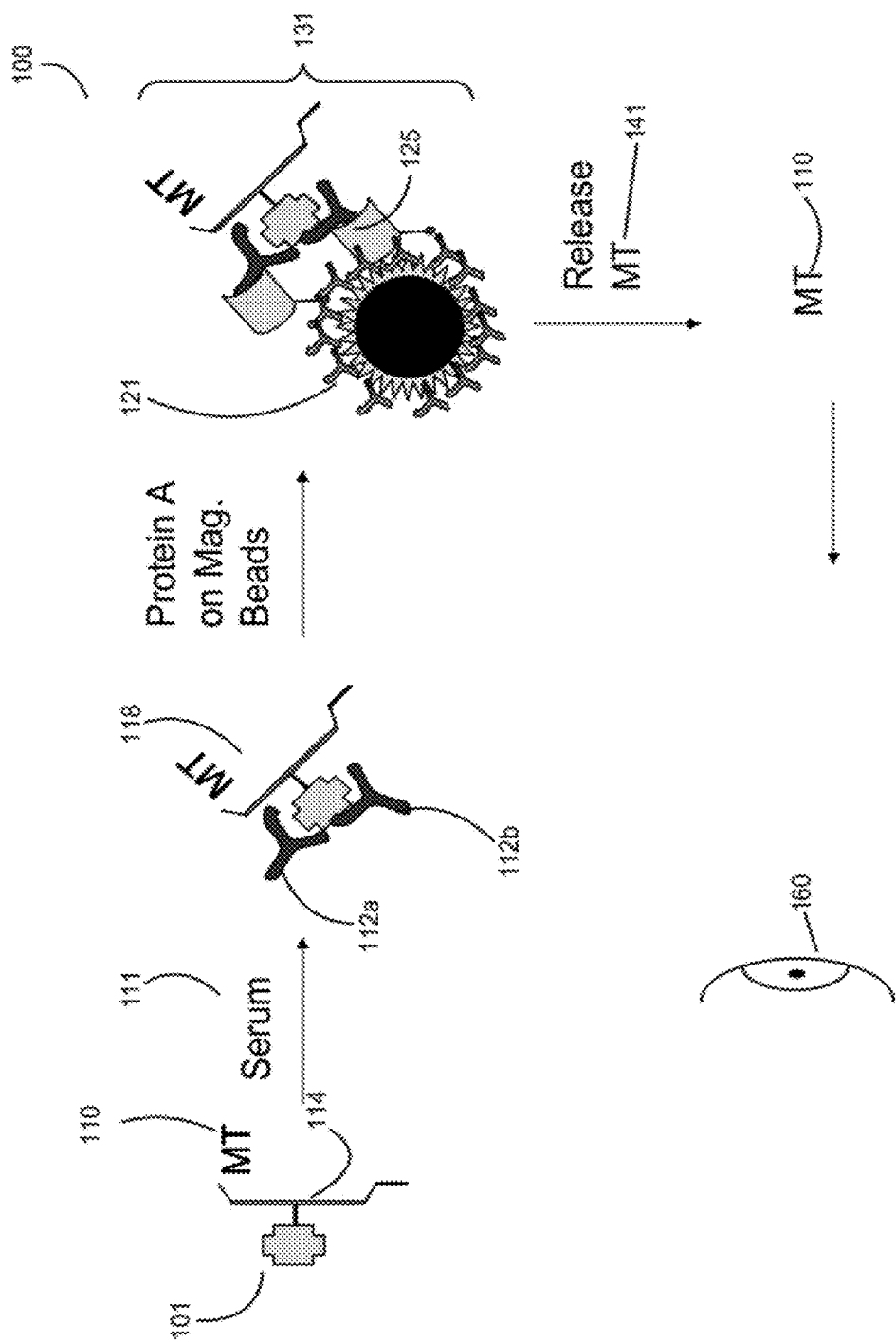
FIG. 1 (A-B) illustrates one embodiment of an assay method of the present invention (Panel A); and Panel B illustrates an alternative assay format.

FIG. 1A is an illustration of one embodiment of an assay method of the present invention. One of ordinary skill in the art will recognize other variations, modifications, and alternatives. As shown therein, the present invention provides an assay method (100) for detecting an autoantibody comprising: contacting a tagged antigen (101) optionally on an antigen support (114) with a sample (111) having an autoantibody (112a, 112b) specific for the tagged antigen (101) to form, or wherein the tagged antigen is transformed into, an immunological pair (118); contacting the immunological pair (118) with a solid support (121) having a binding member (125) specific for the immunological pair (118) to form, or wherein the immunological pair is transformed into, a protein complex (131); separating the protein complex from the sample to form an isolated protein complex; and releasing the tag (141) from the isolated protein complex for detection (160). The tag is preferably a mass tag (110). In certain instances, the antigen support is a hydrophilic molecule, such as a polymer. Suitable polymers include, but are not limited to, polyethylene glycol, dextran, dextran carboxylic acid polyvinyl pyrrolidone, sugar alcohols, polyoxyethylene polyoxypropylene glycol, and a mixture thereof. Dextran is an especially preferred polymer of the present invention.

In certain aspects, the antigen is attached to the antigen support with a "quick-attach" antigen linker. As used herein, the term "quick attach" includes a method or system wherein the antigen support has conjugated thereon a first binding member (e.g., neutravidin) and the antigen has the second binding member attached (e.g., biotin). In this way, the antigen support can be used to attach various antigens in a facile and quick manner.

As used herein, "antigen" and "autoantibody" are each a member of a specific immunological pair. That is, an antigen and an autoantibody are two different molecules wherein one of the molecules (e.g., antigen) through chemical or physical means specifically binds to the second molecule (e.g., autoantibody). An antigen and an autoantibody form an immunological pair. Furthermore, other immunological pairs can include members that are analogs of the original immunological pair, for example, an analyte analog or autoantibody analog. Specific members of the immunological pair include antigens, antigen fragments, antigen analogs, antibodies, antibody fragments, antibody analogs of both monoclonal and polyclonal antibodies and complexes thereof. These include complete immunoglobulins or fragments thereof, and include the various classes and isotypes, such as IgA, IgD, IgE, IgG1, IgG2a, IgG2b, IgG3, and IgM.

The solid support (or solid phase) can be chosen for its intrinsic ability to attract and immobilize the immunological pair. Preferably, the solid phase can retain an additional receptor or binding member which has the ability to attract and subsequently immobilize the immunological pair. The additional receptor or binding member can include a charged substance that is oppositely charged with respect to the immunological pair itself, or to a charged substance conjugated to the immunological pair. In certain aspects, the binding member is immobilized upon (attached to) the solid phase, which has the ability to immobilize the immunological pair through a specific binding reaction. The attachment of the binding member to the solid phase utilizes conventional methods. The binding member enables the binding of the immunological pair to the solid phase material before the performance of the assay or during the performance of the assay. The solid phase or support thus can be a plastic, derivatized plastic, magnetic or non-magnetic metal, glass, or silicon surface of a test tube, microtiter well, sheet, bead, microparticle, chip, and other configurations known to those of ordinary skill in the art.

Further examples of solid phases or supports used in the diagnostic immunoassays of the present invention include porous and non-porous materials, latex particles, magnetic particles, microparticles (see, U.S. Pat. No. 5,705,330), beads, membranes, microtiter wells, and plastic tubes. The choice of the solid phase material and the method of labeling the antigen is determined based upon desired assay format performance characteristics. In certain preferred aspects, the solid support is polystyrene, cellulose, nitrocellulose, a glass bead, or a magnetic bead. A magnetic bead is especially preferred.

Various binding members are suitable for use in the present invention. The binding members are specific for the immunological pair, and preferably attach to the solid support. Suitable binding members include, for example, an antigen, an antibody, biotin, avidin, streptavidin, anti-biotin, folate, folate-binding protein, IgG, Protein A, Protein G, Protein L, a carbohydrate, lectin, and a nucleic acid. In certain aspects, the binding member is a protein which binds to the immunological pair. The protein is preferably Protein A.

In certain aspects, the test sample, or sample, used in the methods of the present invention include biological fluids from a subject. Suitable biological fluids include, but are not limited to, whole blood, serum, plasma, cerebral spinal fluid, urine, seminal fluid, saliva, nipple aspirate, lymph, fine needle aspirate, and any other body constituent or tissue culture supernatant that might contain autoantibodies.

In certain aspects, the protein complex (131) is separated from a subject sample or supernatant to form an isolated protein complex. The release of the mass tag (141) enables detection (160), preferably by mass spectrometric techniques. In preferred aspects, the subject is a mammal. In an especially preferred aspect, the mammal is a human.

Figure 1B:
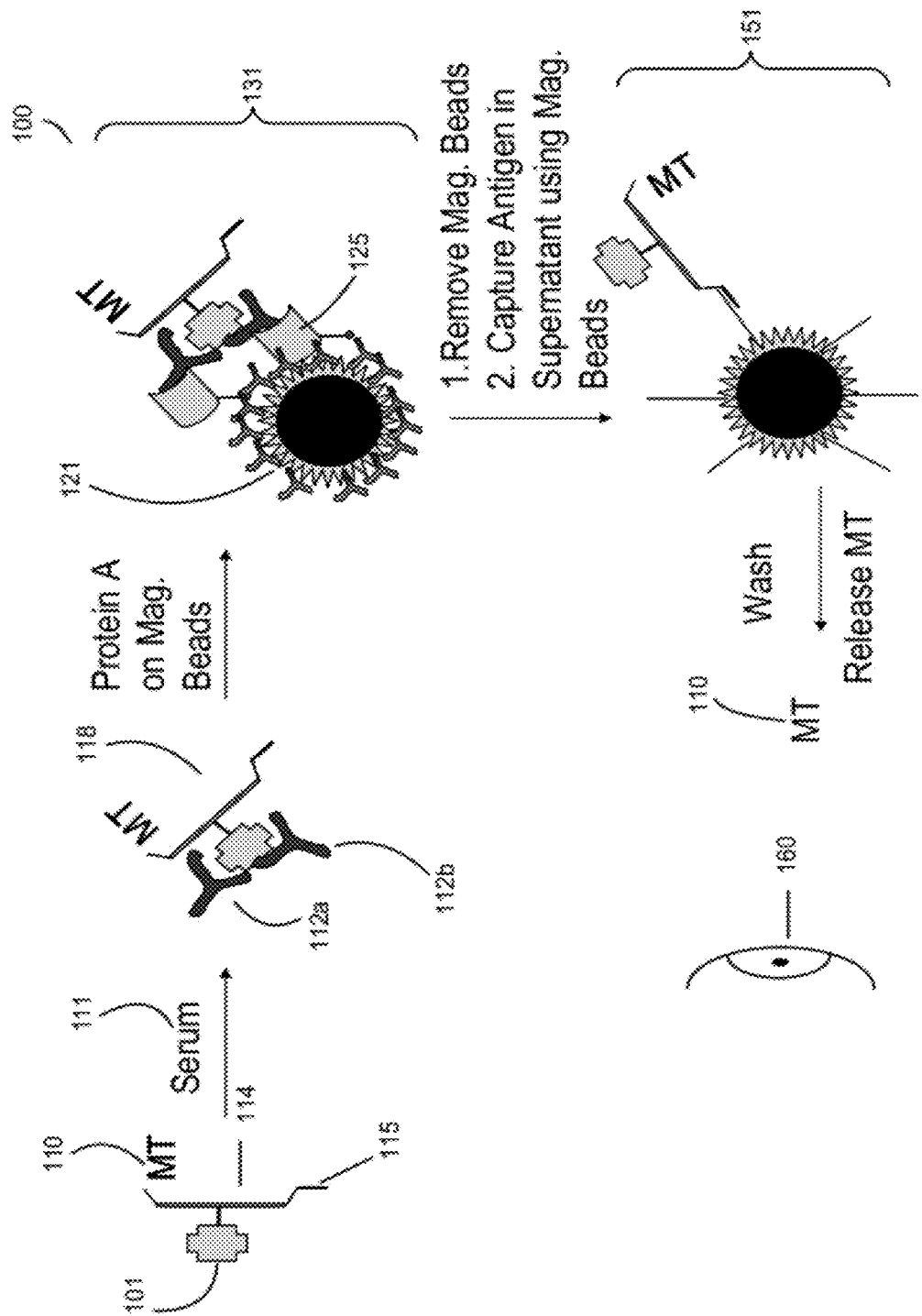

FIG. 1B illustrates a variation of the previous embodiment. In this aspect, the antigen support (114) possesses a linker (e.g., oligonucleotide) (115) such that a solid support complex (151) can form after the formation of the protein complex (131). The mass tag (110) is releasably attached or easily cleavable to the antigen and is able to be detected (160).

Figure 2A:
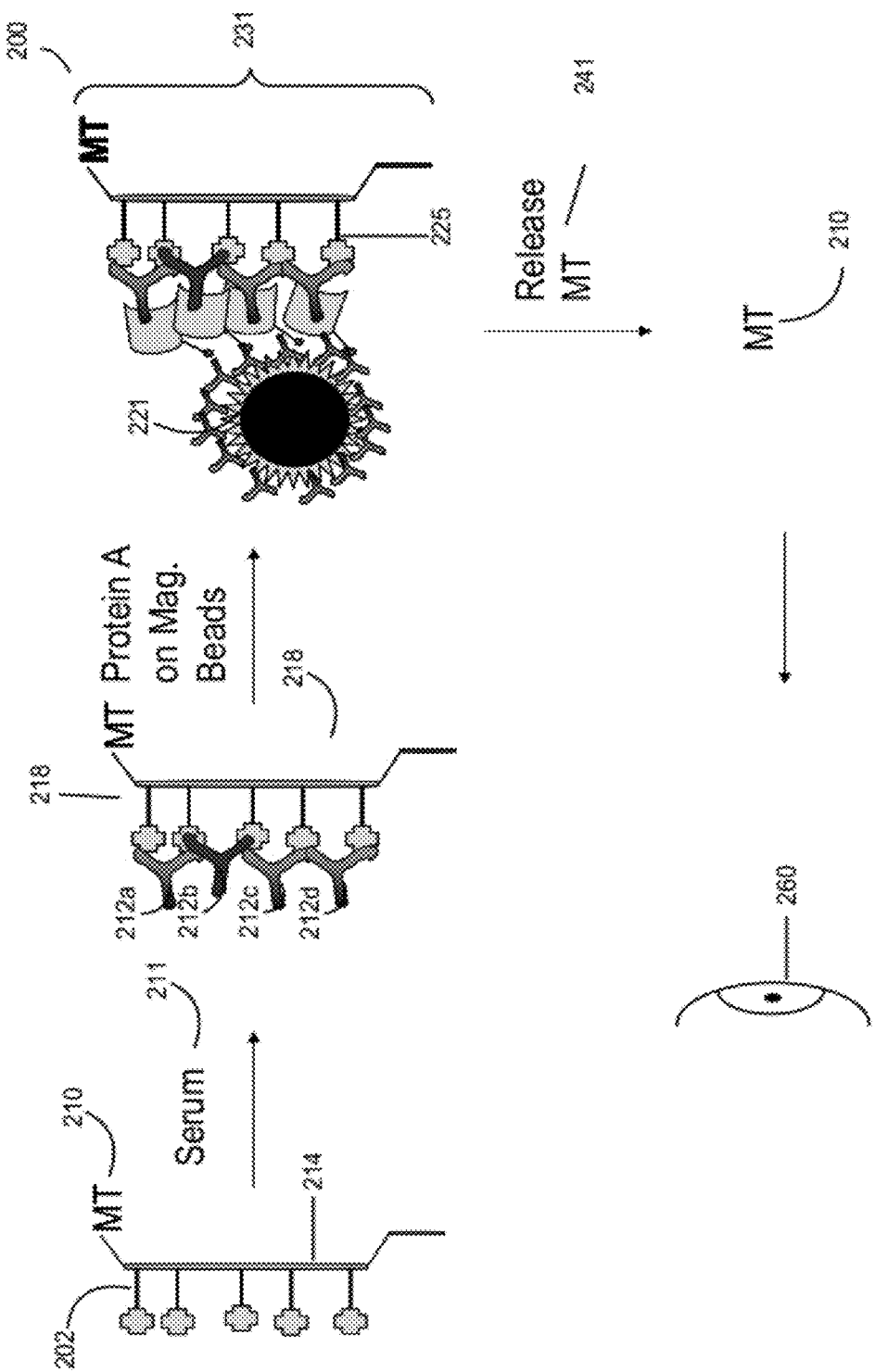
FIG. 2 (A-B) illustrates one embodiment of an assay method of the present invention (Panel A); and Panel B illustrates an alternative assay format.

FIG. 2A is an illustration of another embodiment (200) of the present invention. One of ordinary skill in the art will recognize other variations, modifications, and alternatives. As shown therein, in certain instances, the present invention provides assay methods wherein the tagged antigen is a plurality of antigens (202) on an antigen support (214). The antigens can be the same or different. The tag is preferably a mass tag (210). In certain instances, the antigen support is a hydrophilic molecule, such as a polymer. Suitable polymers include, but are not limited to, polyethylene glycol, dextran, dextran carboxylic acid polyvinyl pyrrolidone, sugar alcohols, polyoxyethylene polyoxypropylene glycol, and a mixture thereof. Dextran is an especially preferred polymer of the present invention.

In certain aspects, the array assay format detects a plurality of autoantibodies (212a-212d) in a sample (211). The plurality of antigens (202) (which may be the same or different) is specific for at least one of the plurality of autoantibodies, which in turn form a plurality of immunological pairs (218). In certain preferred instances, the increase in affinity from the formation of a plurality of immunological pairs (218) allows for increased detection of a single immunological pair. The avidity of a weak antibody is increased, for example IgG can bind two antigens on the hydrophilic support, while IgM can bind as many as six antigens on a hydrophilic support. Thus multiple binding events increase the binding avidity of the autoantibody to the antigen on the hydrophilic polymer support and allow one to detect autoantibodies with weak affinities. The plurality of immunological pairs (218) forms, and a solid support (221) is added having a binding member (225) specific for the plurality of immunological pairs (218) to form a protein complex (231). Thereafter, the protein complex (231) is separated from the sample and the tag is released (241) for detection (260). The detection of multiple autoantibodies aids in differentiating specific autoimmune diseases because each disease can have a unique autoantibody profile.

Figure 2B:
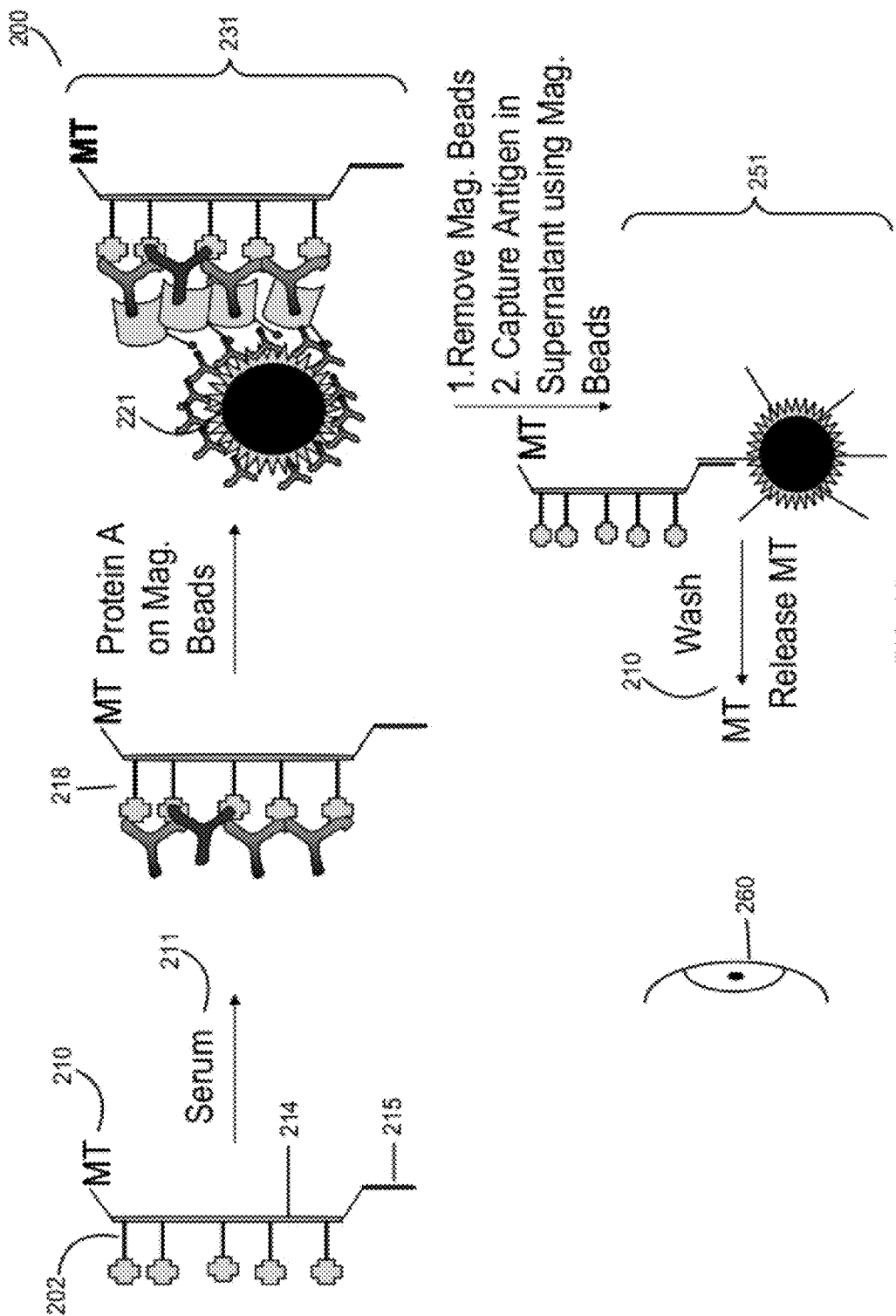

FIG. 2B illustrates a variation of the previous embodiment. In this aspect, the antigen support (214) possesses a linker (e.g., oligonucleotide) (215) such that a solid support complex (251) can form after the formation of the protein complex (231). The mass tag (210) is releasably attached to the antigen and thereafter is detected.

Figure 3A:
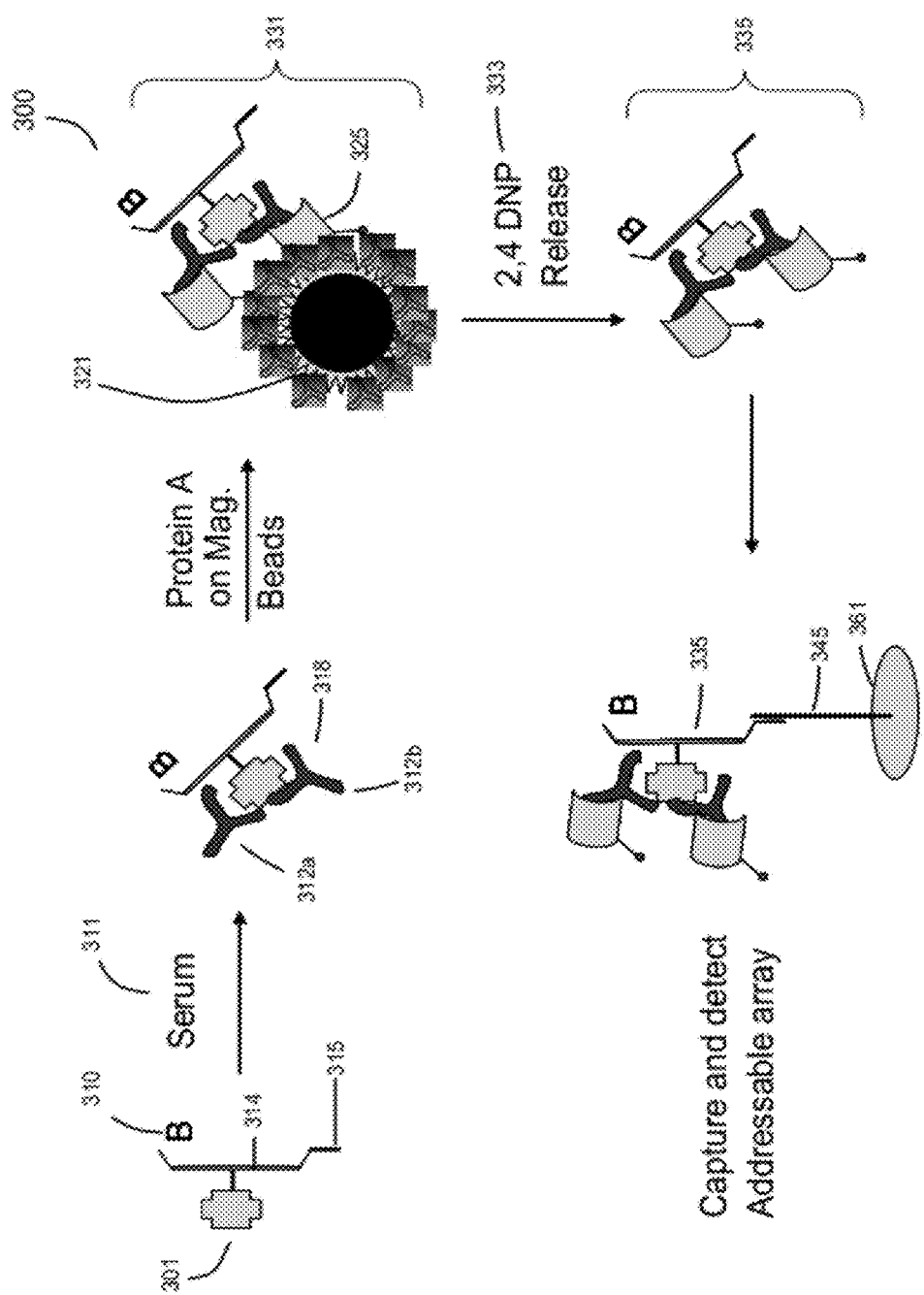
FIG. 3 (A-B) illustrates one embodiment of an assay method of the present invention (Panel A); and Panel B illustrates an alternative assay format.

FIG. 3A is an illustration of one embodiment of the present invention. This diagram is merely an illustration and should not limit the scope of the claims herein. One of ordinary skill in the art will recognize other variations, modifications, and alternatives. As shown therein, the present invention provides an assay method (300) for detecting an autoantibody comprising: contacting a tagged antigen (301) optionally on an antigen support (314) with a sample (311) having an autoantibody (312a, 312b) specific for the tagged antigen (301) to form, or wherein the tagged antigen is transformed into, an immunological pair (318); contacting the immunological pair (318) with a solid support (321) having a binding member (325) specific for the immunological pair (318) to form, or wherein the immunological pair is transformed into, a protein complex (331); separating the protein complex (331) from the sample to form an isolated protein complex; and releasing a solid support (321) from the protein complex to form an immunological pair with a binding member attached (335). The release of the solid support can be achieved by, for example, 2,4 dinitrophenyl hydrazine (2,4 DNP) (333).

Advantageously, the immunological pair with a binding member attached (335) can be captured and detected using an addressable array (361). As used herein, the term "addressable array" includes a spatially or physically ordered array, wherein the immunological pair with a binding member attached (335) is captured. An array includes a collection of elements, such as autoantibodies, containing two or more members. An addressable array is one in which the members of the array are identifiable, typically by position on a solid phase support. In general, the members of the array are immobilized on discrete identifiable loci on the surface of a solid phase (361). In a preferred aspect, the immunological pair with a binding member attached (335) is captured using, for example, an oligonucleotide having a defined sequence (315). The complement of the oligonucleotide (345) is attached to the addressable array (361). In this manner, the antigen is known by its specific oligonucleotide sequence (315) and once attached in a defined location can be identified.

In certain instances, identification of the presence of the immunological pair with a binding member attached (335) is by a detectable moiety "B" (310). The detectable moiety is preferably a fluorescence moiety.

In another embodiment, the detectable moiety "B" (310) comprises a first member of a binding pair (e.g., biotin). A second member of the binding pair (e.g., streptavidin) is attached to a first member of a signal amplification pair. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected, or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

Figure 3B:
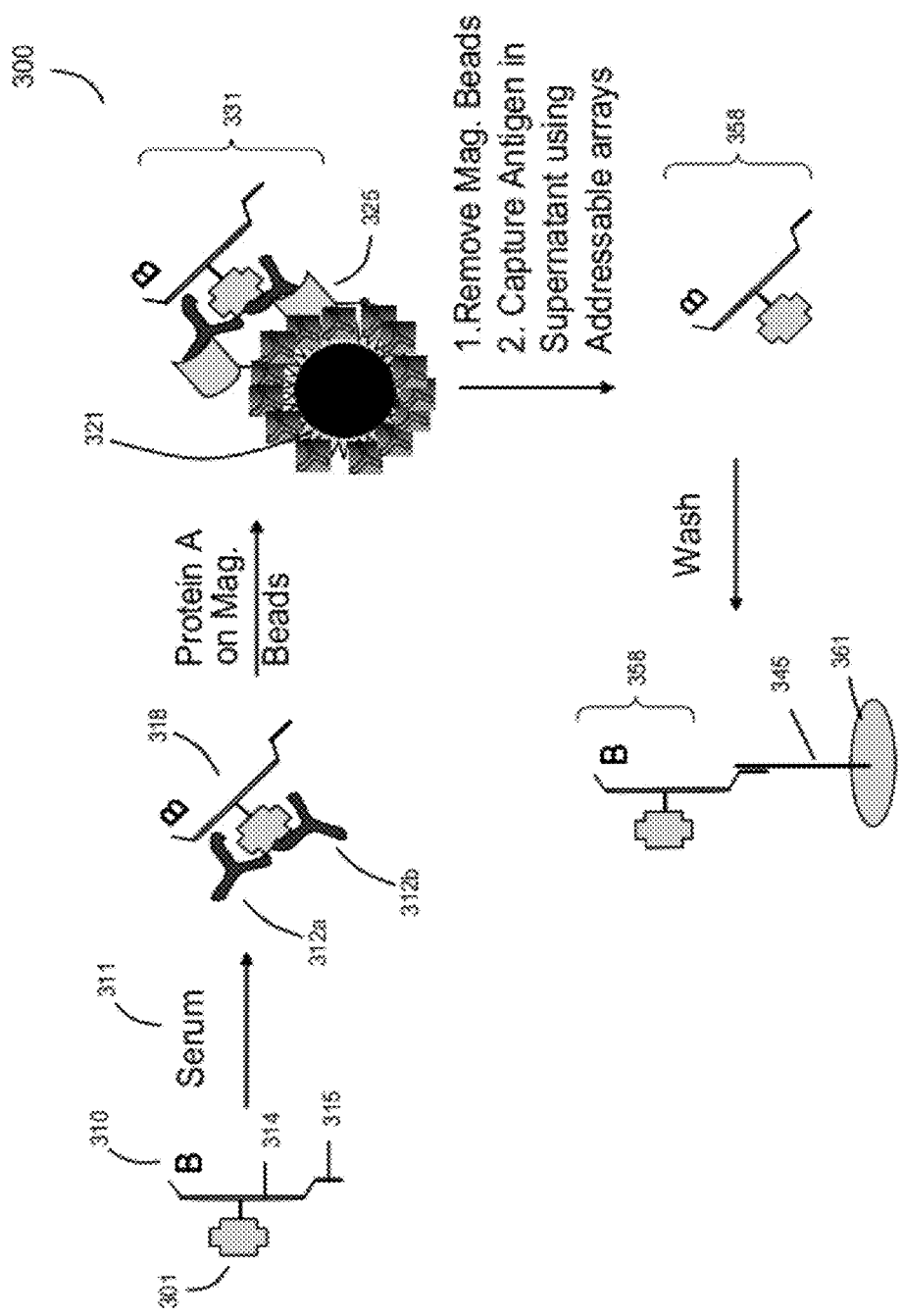

FIG. 3B illustrates a variation of the previous embodiment. In this aspect, the antigen (301) is released from the protein complex (331). The antigen after release (358) is detected using the detectable moiety "B" (310). The detectable moiety is preferably a fluorescence moiety. Again, the members of the array are immobilized on discrete identifiable loci on the surface of a solid phase (361). In a preferred aspect, the released antigen (358) is captured using, for example, an oligonucleotide having a defined sequence (315). The complement of the oligonucleotide (345) is attached to the addressable array (361).

Figure 4A:
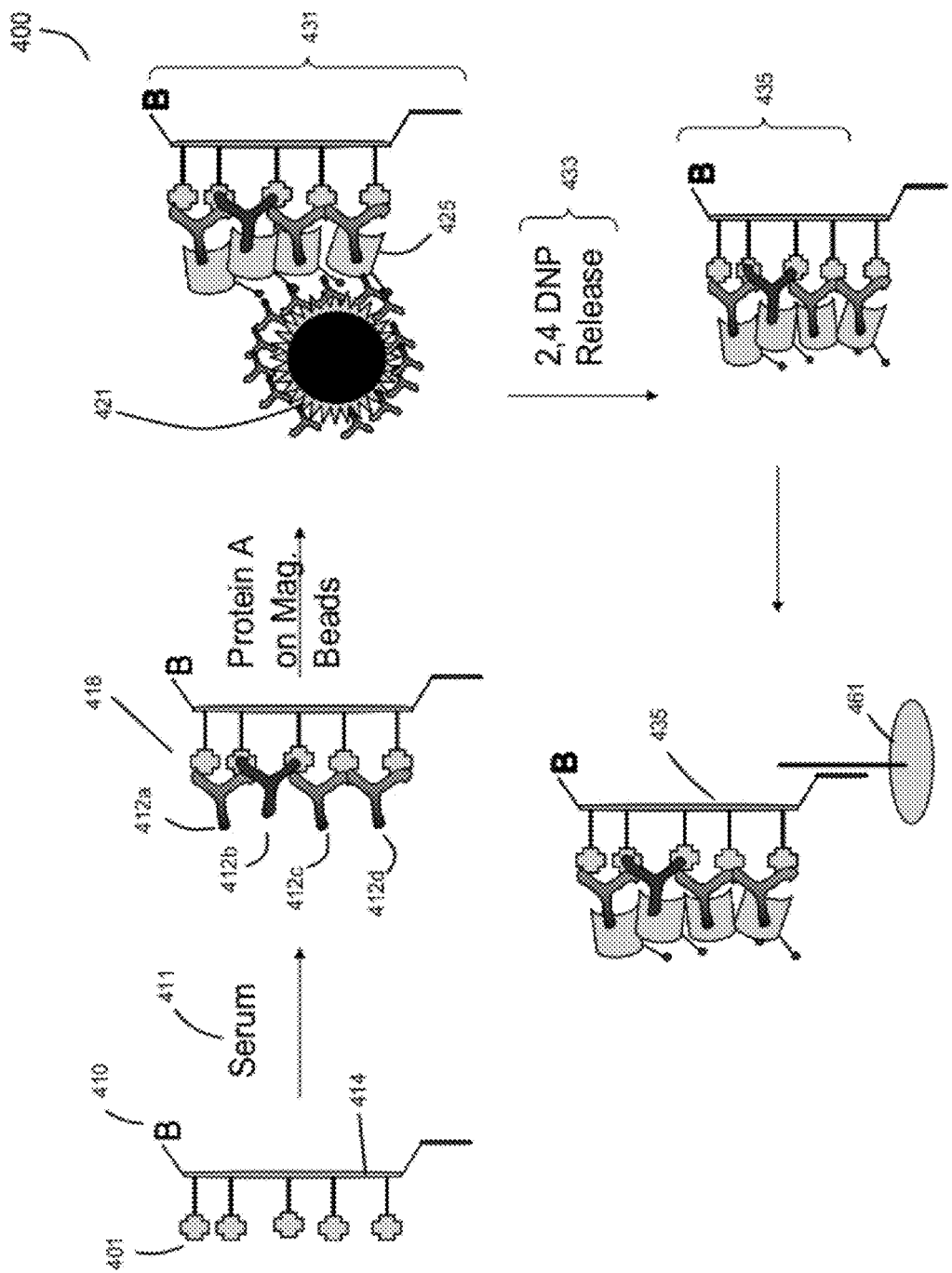
FIG. 4 (A-B) illustrates one embodiment of an assay method of the present invention (Panel A); and Panel B illustrates an alternative assay format.

FIG. 4A illustrates one embodiment of the present invention for detecting a plurality of autoantibodies (412a-412d) which may be the same or different. The plurality of antigens (401) on an antigen support (414) is specific for the plurality of autoantibodies, which in turn form a plurality of immunological pairs (418). In certain preferred instances, the increase in affinity from the formation of a plurality of immunological pairs (418) allows for increased detection of a single immunological pair. The plurality of immunological pairs (418) forms, and a solid support (421) is added having a binding member (425) specific for the plurality of immunological pairs (418) to form a protein complex (431). A plurality of immunological pairs with a binding member attached (435) is released (433) from the protein complex (431) and thereafter captured and detected using an addressable array (461).

In certain instances, identification of the presence of the plurality of immunological pairs with a binding member attached (435) is by a detectable moiety "B" (410). The detectable moiety is preferably a fluorescence moiety.

Figure 4B:
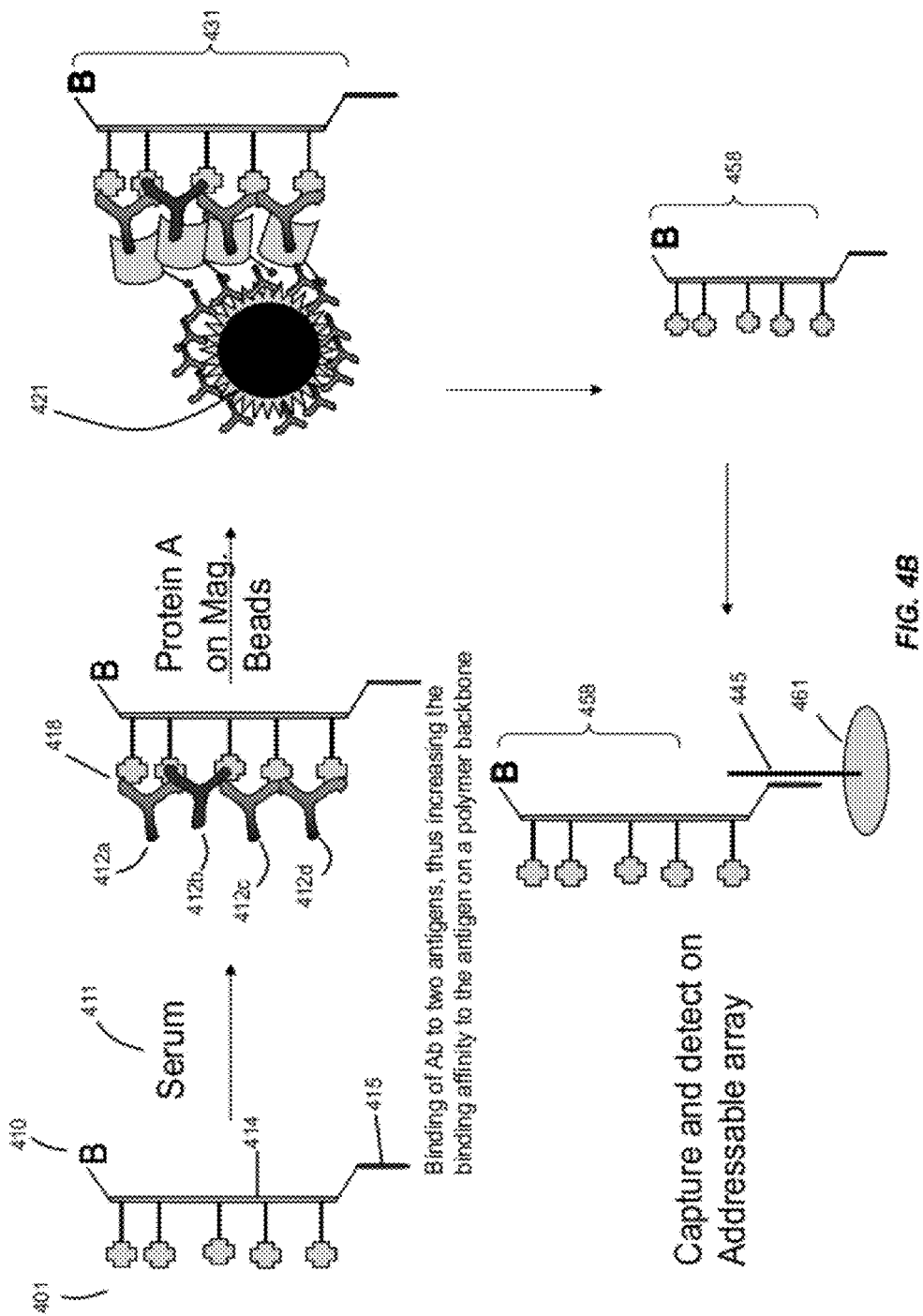

FIG. 4B illustrates a variation of the previous embodiment. In this aspect, the plurality of antigens (401) is released from the protein complex (431). The plurality of antigens after release (458) is detected using the detectable moiety "B" (410). The detectable moiety is preferably a fluorescence moiety. Again, the members of the array are immobilized on discrete identifiable loci on the surface of a solid phase (461). In a preferred aspect, the plurality of antigens after release (458) is captured using, for example, an oligonucleotide having a defined sequence (415). The complement of the oligonucleotide (445) is attached to the addressable array (461).

Figure 5A:
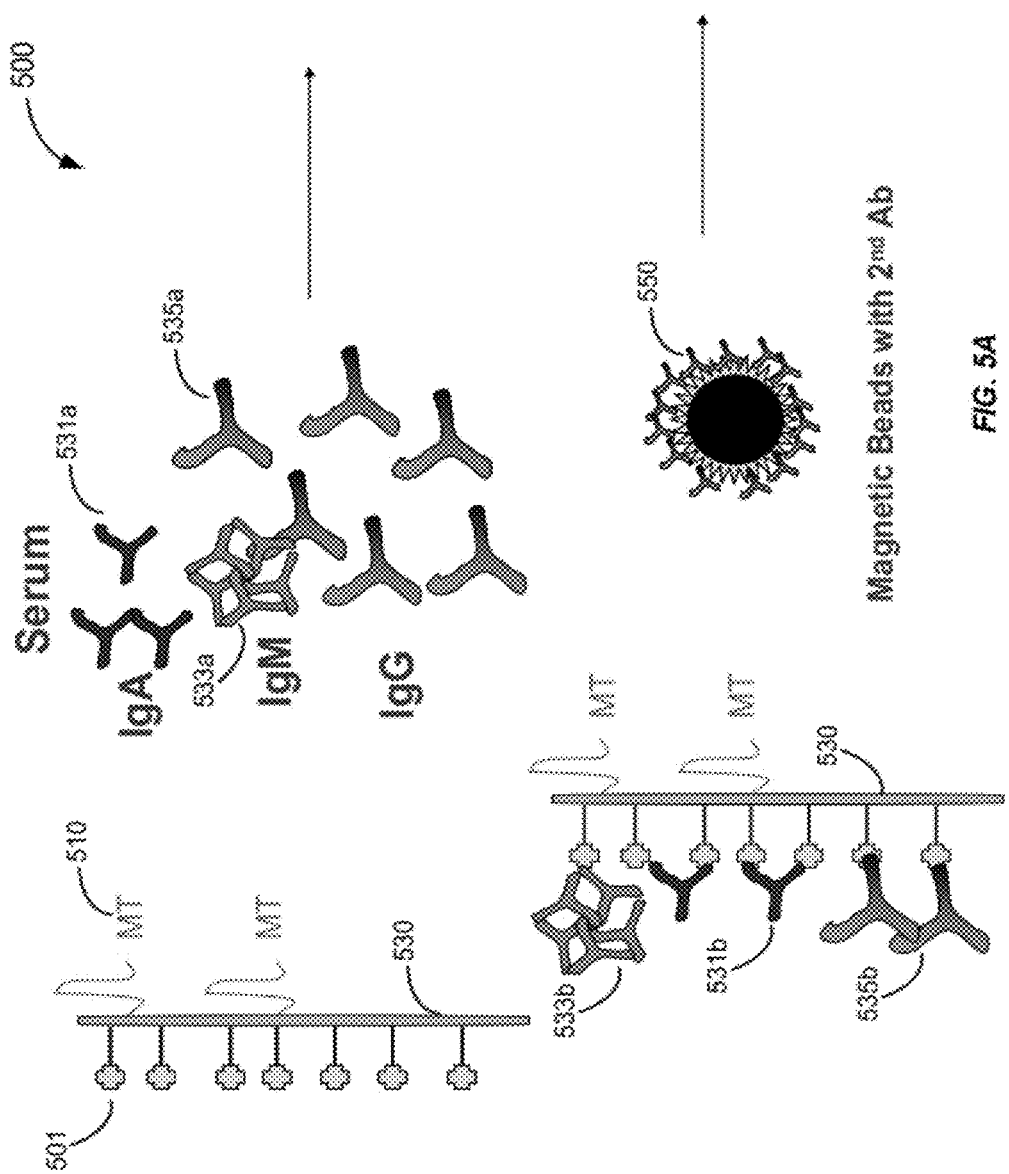
FIG. 5 (A-B) illustrates one embodiment of an assay method of the present invention (Panel A); Panel B illustrates a quantitation step.
Figure 5B:
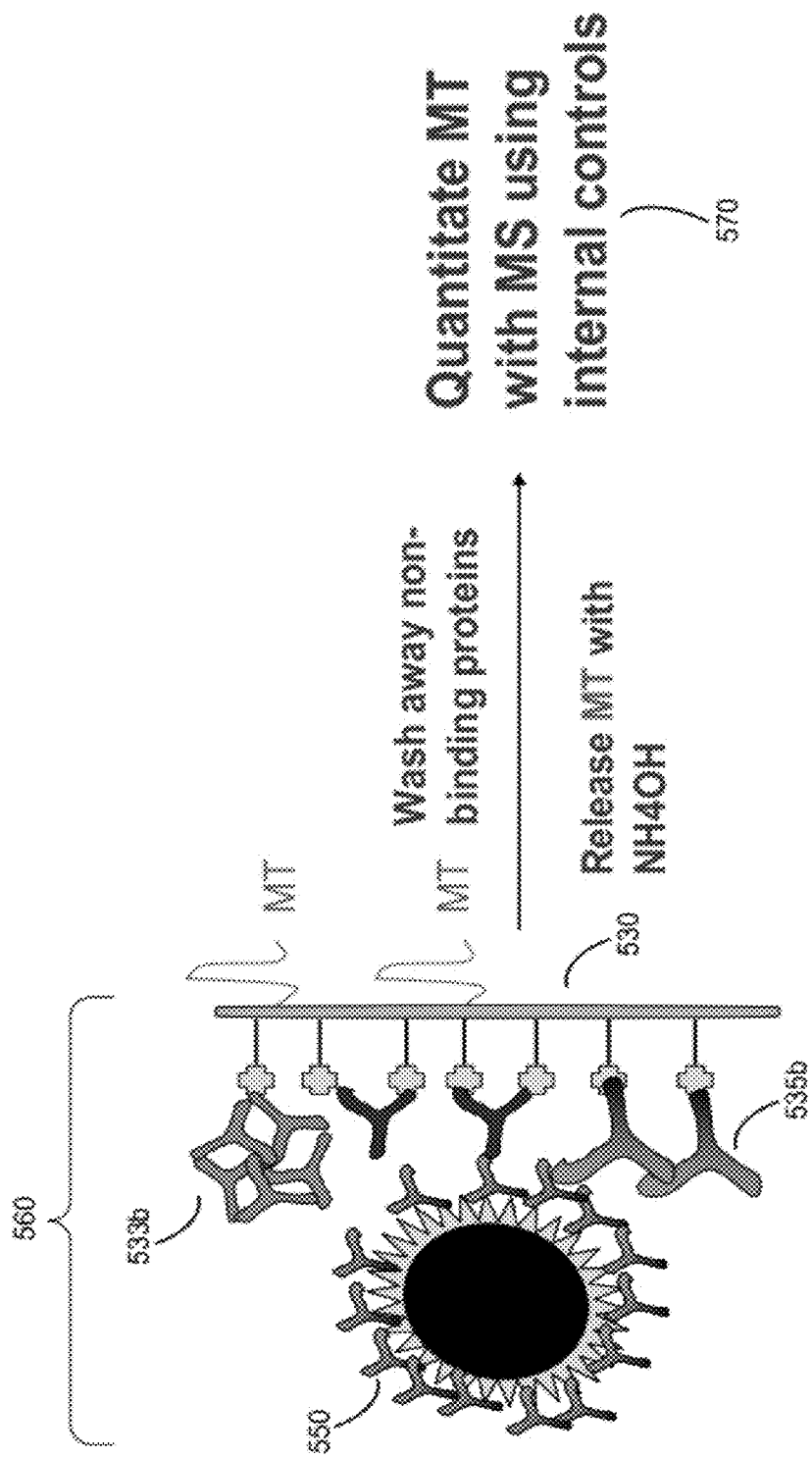

FIG. 5A illustrates one embodiment 500 of the present invention for detecting a plurality of autoantibodies e.g., IgA, IgM, and IgG (531a, 533a, 535a). The plurality of antigens (501) on an antigen support (530) is specific for each of the plurality of autoantibodies, which in turn form, or wherein the plurality if antigens are transformed into, a plurality of immunological pairs (531b, 533b, 535b). After the formation of immunological pairs, a solid support is added having a binding member (550) specific for at least one of the plurality of immunological pairs (531b, 533b, 535b) to form, or wherein the immunological pairs are transformed into, a protein complex (560, FIG. 5B). After washing away non-binding proteins, the mass tags are released with, for example, ammonium hydroxide. The mass tags can be quantitated using for example, internal controls and mass spectrometry (570).

As used herein, an antigen preferably is a biomolecule. An antigen can also be, without limitation, an intact cell or a component of the cell. However, an antigen can also be a small molecule (e.g., steroid, pharmaceutical drug, etc.). A small molecule is considered a non-peptide compound with a molecular weight of less than 500 daltons. Although the antigen in a preferred embodiment of the present invention is an organic molecule, and more preferably a biomolecule, antigens in other embodiments of this invention are non-biomolecules, including, but not limited to, minerals, toxic inorganic compounds, inorganic pollutants, non-biological allergens, and the like.

Thus, for example, a small molecule can be a human-derived steroid hormone such as, but not limited to, adrenalin, noradrenalin, glucocorticoid, mineralocorticoid, cortical sex hormone, androgen (e.g., testosterone), estrogen (e.g., estradiol), or progestin (e.g., progesterone).

Examples of antigens include, but are not limited to, bacteria, viruses, and polynucleotides. Particularly useful antigens are, for example, proteins, carbohydrates, and lipids whose presence or levels correlate with a disease or disorder. The presence or levels of such antigens may correlate with the risk, onset, progression, amelioration, and/or remission of a disease or disorder.

Accordingly, the antigen can be a protein, peptide, amino acid, nucleic acid, carbohydrate, or lipid, including a fatty acid. In one preferred embodiment, the antigen is a polypeptide having a modification such as, but not limited to, phosphorylation, glycosylation, or acylation. In another embodiment, the antigen is a synthetic peptide, oligonucleotide, or fatty acid.

In a particular embodiment, the antigen is a human-derived hormone such as, but not limited to, gastrin, secretin, cholecystokinin, insulin, glucagon, thyroxine triiodothyronine, calcitonin, parathyroid hormone, thymosin, releasing hormones, oxytocin, vasopressin, growth hormone, prolactin, melanophore-stimulating hormone, thyrotrophic hormone, adrenocorticotrophic hormone, follicle-stimulating hormone, luteinizing hormone, or melatonin.

In one embodiment, the antigen is a marker for a disease or disorder. Such disease or disorder can be, without limitation, an allergy, anxiety disorder, autoimmune disease, behavioral disorder, birth defect, blood disorder, bone disease, cancer, circulatory disease, tooth disease, depressive disorder, dissociative disorder, ear condition, eating disorder, eye condition, food allergy, food-borne illness, gastrointestinal disease, genetic disorder, heart disease, hormonal disorder, immune deficiency, infectious disease, inflammatory disease or disorder, insect-transmitted disease, nutritional disorder, kidney disease, leukodystrophy, liver disease, mental health disorder, metabolic disease, mood disorder, musculodegenerative disorder, neurological disorder, neurodegenerative disorder, neuromuscular disorder, personality disorder, phobia, pregnancy complication, prion disease, prostate disease, psychological disorder, psychiatric disorder, respiratory disease, sexual disorder, skin condition, sleep disorder, speech-language disorder, sports injury, tropical disease, vestibular disorder, or wasting disease.

In another embodiment, the antigen is a marker for an autoimmune disease such as, but not limited to, Addison's disease, alopecia greata, ankylosing spondylitis, antiphospholipid syndrome (APS), Behcet's disease, chronic fatigue syndrome, Crohn's disease and ulcerative colitis, fibromyalgia, Goodpasture syndrome, graft versus host disease, lupus (e.g., systemic lupus erythematosus), Meniere's disease, multiple sclerosis, myasthenia gravis, myositis, pemphigus vulgaris, psoriasis, rheumatic fever, sarcoidosis, scleroderma, vasculitis, vitiligo, or Wegener's granulomatosis.

In another embodiment, the antigen is a marker for cancer such as, but not limited to, non-Hodgkin's lymphoma, Hodgkin's lymphoma, leukemia (e.g., acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatic cancer, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system; and other tumor types and subtypes (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

In another embodiment, the antigen is a marker for an infection or infectious disease such as, but not limited to, acquired immunodeficiency syndrome (AIDS/HIV) or HIV-related disorders, Alpers syndrome, anthrax, bovine spongiform encephalopathy, (BSE), chicken pox, cholera, conjunctivitis, Creutzfeldt-Jakob disease (CJD), dengue fever, ebola, elephantiasis, encephalitis, fatal familial insomnia, Fifth's disease, Gerstmann-Straussler-Scheinker syndrome, hantavirus, *helicobacter pylori*, hepatitis (hepatitis A, hepatitis B, hepatitis C), herpes, influenza, Kuru, leprosy, lyme disease, malaria, hemorrhagic fever (e.g., Rift Valley fever, Crimean-Congo hemorrhagic fever, Lassa fever, Marburg virus disease, and Ebola hemorrhagic fever), measles, meningitis (viral, bacterial), mononucleosis, nosocomial infections, otitis media, pelvic inflammatory disease (PID), plague, pneumonia, polio, prion disease, rabies, rheumatic fever, roseola, Ross River virus infection, rubella, salmonellosis, septic arthritis, sexually transmitted diseases (STDs), shingles, smallpox, strep throat, tetanus, toxic shock syndrome, toxoplasmosis, trachoma, tuberculosis, tularemia, typhoid fever, valley fever, whooping cough, or yellow fever.

In another embodiment, the antigen is a marker for a bone disease such as, but not limited to, achondroplasia, bone cancer, fibrodysplasia ossificans progressiva, fibrous dysplasia, Legg-Calve-Perthes disease, myeloma, osteoarthritis, osteogenesis imperfecta, osteoporosis, Paget's disease, or scoliosis.

In another embodiment, the antigen is a marker for a circulatory disease such as, but not limited to, elephantiasis, heart disease, hemochromatosis, hemophilia, hypertension, hypotension, Klippel-Trenaunay-Weber syndrome, lymphedema, neutropenia, peripheral vascular disease (PVD), phlebitis, Raynaud's phenomenon, thrombosis, twin-to-twin transfusion syndrome, or vasculitis.

In another embodiment, the antigen is a marker for a metabolic disease such as, but not limited to, acid maltase deficiency, diabetes, galactosemia, hypoglycenia, Lesch-Nyhan syndrome, maple syrup urine disease (MSUD), Niemann-Pick disease, phenylketonuria, or urea cycle disorder.

In another embodiment, the antigen is a marker for a nutrition or gastrointestinal disorder such as, but not limited to, appendicitis, botulism, canker sores, celiac disease, colitis (including uLcerative colitis), cyclic vomiting syndrome (CVS), diarrhea, hiatus hernia, inflammatory bowel disease (IBD), irritable bowel syndrome (IBS), peptic ulcer, primary biliary cirrhosis, salinonellosis, anorexia nervosa, bulimia nervosa, bovine spongiform encephalopathy (BSE), Fugu poisoning, or diverticulitis.

In another embodiment, the antigen is a marker for an ear disorder such as, but not limited to, acoustic neuroma, cholesteatoma, deafness, mastoiditis, Meniere's disease, otitis, tinnitus, or a vestibular disorder.

In another embodiment, the antigen is a marker for an eye disorder such as, but not limited to, amblyopia, cataract, color blindness, conjunctivitis, glaucoma, keratoconus, macular degeneration, microphthalmia, anophthalmia, retinitis pigmentosa, retinoblastoma; strabismus, or trachoma.

In another embodiment, the antigen can be a marker for a genetic disorder such as, but not limited to, achondroplasia, achromatopsia, acid maltase deficiency, adrerioleukodystrophy, Aicardi syndrome, alpha-1 antitrypsin deficiency, androgen insensitivity syndrome, Apert syndrome, arrhythmogenic right ventricular dysplasia, ataxia relangiectasia, Canavan disease, Cri Du Chat syndrome, cystic fibrosis, Dercum's disease, familial adenomatous polyposis, familial breast cancer susceptibility, Fanconi anemia, fragile X, syndrome, galactosemia, Gaucher disease, hemochromatosis, Huntington's disease, Hurler syndrome, hypophosphatasia, Klinefelter syndrome, Krabbes disease, Langer-Giedion syndrome, leukodystrophy, long QT syndrome, Marfan syndrome, Moebius syndrome, mucopolysaccharidosis (MPS), nail patella syndrome, nephrogenic diabetes insipidus, porphyria, non-hereditary polyposis colorectal cancer (NHPCC), Prader-Willi syndrome, progeria, Proteus syndrome, Rett syndrome, Rubinstein-Taybi syndrome, Sanfilippo syndrome, Shwachman syndrome, Smith-Magenis syndrome, Stickler syndrome, Tay-Sachs disease, Treacher Collins syndrome, triose phosphate isomerase deficiency, trisomy, tuberous sclerosis, Turner's syndrome, urea cycle disorder, Williams syndrome, Wilson's disease, or angina pectoris.

In another embodiment, the antigen can be a marker for a heart disease such as, but not limited to, arrhythmogenic right ventricular dysplasia, atherosclerosis/arteriosclerosis, cardiomyopathy, congenital heart disease, endocarditis, enlarged heart, heart attack, heart failure, heart murmur, heart palpitations, high cholesterol, high tryglycerides, hypertension, long QT syndrome, mitral valve prolapse, postural orthostatic tachycardia syndrome, tetralogy of fallots, or thrombosis.

In another embodiment, the antigen can be a marker for a kidney disorder such as, but not limited to, kidney cancer, kidney infection, kidney stones, kidney transplants, nephrogenic diabetes insipidus, nephrology, or rhabdomyolysis.

In another embodiment, the antigen can be a marker for a leukodystrophy such as, but not limited to, adrenoleukodystrophy and Krabbes disease.

In another embodiment, the antigen can be a marker for a liver disorder such as, but not limited to, alpha-1 antitrypsin deficiency, Gilbert's syndrome, hepatitis, or liver cancer.

In another embodiment, the antigen can be a marker for a mood disorder such as, but not limited to, bipolar disorder (manic depression), depressive disorder, or seasonal affective disorder.

In another embodiment, the antigen can be a marker for a neurological or musculoskeletal disorder such as, but not limited to, Aicardi syndrome, Alzheimer's disease, amnesia, amyotrophic lateral sclerosis (Lou Gehrig's Disease), anencephaly, aphasia, arachnoiditis, Arnold Chiari malformation, ataxia telangiectasia, Batten disease, Bell's palsy, brachial plexus injury, brain injury, brain tumor, Charcol-Marie-Tooth disease, encephalitis, epilepsy, essential tremor, Guillain-Barre Syndrome, hydrocephalus, hyperhidrosis, Krabbes disease, meningitis, Moebius syndrome, muscular dystrophy, multiple sclerosis, Parkinson's disease, peripheral neuropathy, postural or orthostatic tachycardia syndrome, progressive supranuclear palsy, Reye's syndrome, shingles, Shy-Drager Syndrome (SDS), spasmodic torticollis, spina bifida, spinal muscular atrophy, Stiff Man syndrome, synesthesia, syringomyelia, thoracic outlet syndrome, Tourette syndrome, toxoplasmosis, or trigeminal neuralgia.

In another embodiment, the antigen can be a marker for a respiratory disease such as, but not limited to, alveolar capillary dysplasia, asthma, black lung, bronchiolitis, chronic obstructive pulmonary disease (COPD), emphysema, laryngeal cancer, laryngomalacia, legionnaires' disease, lung cancer, lymphagioleiomyomatosis (LAM), pleurisy (pleuritis), pneumonia, respiratory distress syndrome, respiratory syncytial virus (RSV), sarcoidosis, silicosis, sinus infection, tonsillitis, tuberculosis, or valley fever.

In another embodiment, the antigen can be a marker for a skin condition such as, but not limited to, chicken pox, chronic hives (urticaria), decubitus ulcer, eczema, Ehlers-Danlos Syndrome, epidermolysis bullosa, gangrene, hidradenitis suppurativa, hot tub folliculitis, hyperhidrosis, ichthyosis, impetigo, keratosis pilaris, leprosy, measles, molluscum contagiosum, pityriasis rosea, porphyria, pseudofolliculitis barbae, psoriasis, rosacea, rubella, scleroderma, shingles, or skin cancer.

An antigen can be a component of a virus such as, but not limited to, herpes simplex virus, cytomegalovirus, Epstein-Barr virus, human immunodeficiency virus-1, adenovirus, rhinovirus, human immunodeficiency virus-2, human papilloma virus, HTLV-I, HTLV-II, or HTLV-III. Also, antigen markers for other conditions can be assayed such as, but not limited to, pregnancy, alcoholism, drug abuse, allergy, poisoning, secondary effects of, or responses to, treatments or secondary effects of diseases.

III. Detection by Mass Spectrometry

A. Mass Tags

In certain instances, the antigen specific for the autoantibody of interest is labeled or tagged with a small organic molecule, such as a mass tag. The mass tag is preferably detected by mass spectrometry. In certain instances, the mass tag is a surrogate for the detection and analysis of the antigen bound to the antibody. The analysis can be quantitative, semi-quantitative, qualitative, or a combination thereof. "Detection" includes identifying the presence, absence, and/or amount of the "mass tag" and by inference the amount of antigen bound to the antibody of interest. "Absence" of binding and "lack of detection of autoantibody" as used herein include insignificant or de minimus levels.

Advantageously, the mass tags described herein are generally unreactive after attached to the antigen. The chemical stability of these tags and their compatibility with a variety of rapid, convenient methods of separation and analysis, such as gas chromatography and mass spectrometry, enables high throughput screening methods. Moreover, the organic tags of the present invention, once attached, generally do not specifically interact with biological materials. Thus, the tags will generally not give spurious results in biological assays and will generally not be modified by other biological molecules.

Figure 6:
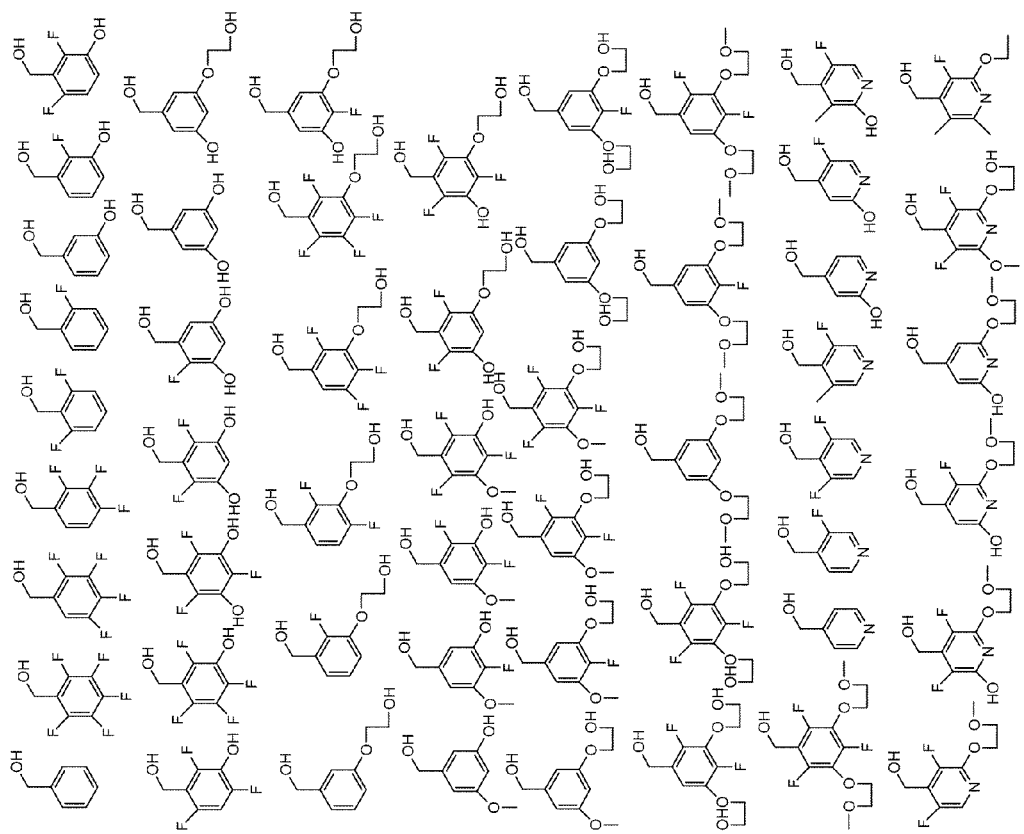
FIG. 6 illustrates various embodiments of mass tags of the present invention.

In one embodiment, the mass tag is a small organic molecule as shown in FIG. 6. One of ordinary skill in the art will recognize other variations, modifications, and alternatives. In certain instances, the mass tag is attached to the antigen specific for the autoantibody of interest. In certain other instances, the mass tag is attached to the antigen support. The attachment can be via complementary functional groups.

Selected examples of reactive functionalities useful for the attaching the mass tag to the antigen or antigen support are shown in Table 1, wherein the link results from the reaction of a mass tag with the antigen (e.g., protein) or antigen support (e.g., dextran). Those of skill in the art will know of other attachments suitable for use in the present invention.

TABLE 1

| A<br>Reactive functionality<br>(either on the mass tag or<br>the antigen/antigen support) | B<br>Complementary group<br>(either on the antigen or<br>the mass tag/antigen support) | C<br>The resulting<br>bond |
| --- | --- | --- |
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | carboxamides/imides |
| aryl halides | thiols | thiophenols |
| aryl halides | amines | aryl amines |
| aziridines | thiols | thioethers |
| boronates | glycols | boronate esters |
| activated carboxylic acids | amines/anilines | carboxamides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |

TABLE 1-continued

| A<br>Reactive functionality<br>(either on the mass tag or<br>the antigen/antigen support) | B<br>Complementary group<br>(either on the antigen or<br>the mass tag/antigen support) | C<br>The resulting<br>bond |
| --- | --- | --- |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

*Activated esters, as understood in the art, generally have the formula —COM, where M is a good leaving group (e.g. succinimidyloxy (—$OC_4H_4O_2$) sulfosuccinimidyloxy (—$OC_4H_3O_2SO_3H$), -1-oxybenzotriazolyl (—$OC_6H_4N_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or $OCNR^aNHR^b$, where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).
**Acyl azides can also rearrange to isocyanates.

In another aspect, the mass tag is attached to the antigen specific for the autoantibody of interest or to the antigen support via a cleavable linkage. Generally, the cleavable linkage connects the mass tag to the antigen or antigen support. The cleavable linkage comprises at least one cleavable moiety and one or more optional linker moieties. The cleavable moiety comprises at least one functional group that can be cleaved to allow detachment of the mass tag from the antigen or antigen support. The optional linker moieties typically comprise one or more linkage groups that can be used to affect the solubility of the mass tag and/or that function to attach the cleavable linkage to the antigen or antigen support and the mass tag.

In certain preferred aspects, the present methods employ tags which are cleavable from the antigen or antigen support. Such cleavability allows the tags to be distinguished on more than one basis; in particular, they can be separated (e.g., on the basis of chromatographic retention time) and then analyzed (e.g., a second basis is a spectral property such as mass spectroscopy or electrophoricity). Further, the chemical stability of the present tags allows them to be cleaved by a wide variety of methods, which improves sensitivity in their analysis. Cleavability further allows tags to be detected at very low levels because they can be removed from the matrix, the presence of which could provide spurious background signals.

The cleavable moiety can comprise any number of functional groups. For example, the cleavable moiety can comprise a functional group that can be cleaved by a selected cleaving agent when the autoantibody is bound to, or interacting with, the antigen. As another example, the cleavable moiety can comprise a functional group that can be cleaved under selected cleaving conditions, or by a selected chemical reaction. Thus, cleavable moieties can include functional groups that can be photolytically, chemically, thermally, or enzymatically cleaved. See, e.g., U.S. Pat. No. 5,721,099; U.S. Patent Publication No. 20040166529; U.S. patent application Ser. No. 10/828,647; and Greene et al., PROTECTIVE GROUPS IN ORGANIC SYNTHESIS, 2nd ed. Wiley, 1991.

In some embodiments, the cleavable moiety comprises silyl groups that can be cleaved with halogens, such as fluoride, bromine or chlorine, by oxidation or acid. In other embodiments, the cleavable moiety can comprise photolabile linkages, such as o-nitrobenzyl, 7-nitroindanyl, 2-nitrobenzhydryl ethers or esters, and the like, that can be cleaved with electromagnetic radiation.

Other examples of cleavable moieties are known to those skilled in the art, for example, catechols, which can be cleaved with cerium salts, can be used as cleavable moieties. Olefins, which can be cleaved with ozone, permanganate or osmium tetroxide, can be used as cleavable moieties. Sulfides, which can be cleaved with singlet oxygen or by enzyme catalyzed oxidative cleavage with hydrogen peroxide, where the resulting sulfone can undergo elimination, can be used as cleavable moieties. Furans, which can be cleaved with oxygen or bromine in methanol, can be used as cleavable moieties. Tertiary alcohols ketals and acetals, which can be cleaved with acid, can be used as cleavable moieties. Alpha- and beta-substituted ethers and esters, which can be cleaved with base, where the substituent is an electron withdrawing group, e.g., sulfone, sulfoxide, ketone, and the like, can be used as cleavable moieties. Substituted benzyl ether or derivatives thereof, e.g., benzhydryl ether, indanyl ether, and the like, which may be cleaved by acidic or mild reductive conditions, can be used as cleavable moieties.

In some embodiments, the cleavable linkage comprises one or more optional linker moieties. The linker moieties can comprise any linkage group capable of connecting the cleavable moiety to another moiety of the antigen or antigen support.

In certain aspects, the linker moiety comprises one or more (bis)ethylene glycol group(s). As will be appreciated by a person skilled in the art, the number of oxyethylene units comprising the linker moiety can be selectively varied. For example, one, two, three or more oxyethylene units may be used to form a linker moiety. Virtually any combination of the same or different oxyethylene units that permits the cleavable linkage to function as described herein may be used. In a specific example, the linker moiety may comprise from 1 to about 5 (1, 2, 3, 4 or 5) of the same or different lower oxyethylene units. The chemical composition of the linker moiety is not critical. Any type of linker moiety that permits the resultant labeling molecule to function as described herein can be used.

A linker moiety can be selected to have specified properties. For example, the linker moiety can be hydrophobic in character, hydrophilic in character, long or short, rigid, semirigid or flexible, depending upon the particular application. The linker moiety can be optionally substituted with one or more substituents or one or more linking groups for the attachment of additional substituents, which may be the same or different, thereby providing a "polyvalent" linking moiety capable of conjugating or linking additional molecules or substances to the labeling molecule. In certain embodiments, however, the linker moiety does not comprise such additional substituents or linking groups.

A wide variety of linker moieties comprised of stable bonds are known in the art, and include by way of example and not limitation, alkyldiyls, substituted alkyldiyls, heteroalkyldiyls, substituted heteroalkyldiyls, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryl diyls, substituted heteroaryl-heteroaryl diyls, heteroarylalkyldiyls, substituted heteroarylalkyldiyls, heteroaryl-heteroalkyldiyls, substituted heteroaryl-heteroalkyldiyls, and the like. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-, 1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, butan-1,2-diyl, butan-1,3-diyl, butan-1,4-diyl, butan-2,2-diyl, 2-methyl-prop-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, and the like. Thus, a linker moiety can include single, double, triple or aromatic carbon-carbon bonds, nitrogen-nitrogen bonds, carbon-nitrogen bonds, carbon-oxygen bonds, carbon-sulfur bonds and combinations of such bonds, and may therefore include functionalities such as carbonyls, ethers, thioethers, carboxamides, sulfonamides, ureas, urethanes, hydrazines, and the like. In some embodiments, the linker moiety has from 1-20 non-hydrogen atoms selected from the group consisting of C, N, O, P, and S and is composed of any combination of ether, thioether, amine, ester, carboxamide, sulfonamides, hydrazide, aromatic, and heteroaromatic groups.

Choosing a linker moiety having properties suitable for a particular application is within the capabilities of those having skill in the art. For example, where a rigid linker moiety is desired, the linker moiety may comprise a rigid polypeptide such as polyproline, a rigid polyunsaturated alkyldiyl or an aryldiyl, biaryldiyl, arylarydiyl, arylalkyldiyl, heteroaryldiyl, biheteroaryldiyl, heteroarylalkyldiyl, heteroaryl-heteroaryldiyl, etc. Where a flexible linker moiety is desired, the linker moiety may comprise a flexible polypeptide such as polyglycine or a flexible saturated alkanyldiyl or heteroalkanyldiyl. Hydrophilic linker moieties may comprise, for example, polyalcohols, polyethers, such as polyalkyleneglycols, or polyelectroyles, such as polyquaternary amines. Hydrophobic linker moieties may comprise, for example, alkyldiyls or aryldiyls.

In certain other embodiments, the mass tag and cleavable linkage are disclosed in U.S. Pat. No. 6,503,759, incorporated herein by reference. Especially preferred mass tags together with a cleavable linker are set forth in columns 12-16 of U.S. Pat. No. 6,503,759.

B. Tag Analysis

Tags can be removed from the antigen or antigen support using reductive, oxidative, thermolytic, hydrolytic, photolytic conditions or other methods known in the art depending on the nature of the linkage. Examples include, but are not limited to, oxidation of a catechol ether with ceric ammonium nitrate, photolysis of a nitrobenzyl ether or ester or amide, or by other methods.

Differentiation of tags can be achieved with physical differences, e.g., molecular weight of the tags, or the chromatographic retention time using gas or liquid chromatography. Positional isomers may have different retention times. If positional isomers or steroisomers are inadequate for physical separation, then one could use varying numbers of substituents, e.g., halogens (such as fluorines), methyl groups, oxy groups, or other side chains in conjunction with differing numbers of units, e.g., methylene groups or ethyleneoxy groups, to provide the desired separation. Ratios of radioisotopes can also be used.

When the tags obtained upon release from the antigen or antigen support have an active functionality, these tags can be reacted with a labeling reagent which introduces a detectable tag. Conveniently, the functionality can be a double bond (particularly an activated double bond), hydroxy, thio, amino, carboxy, and the like. The tag would then be reacted with an excess of the labeling reagent to provide a detectable product for analysis. In this way a wide variety of labeling reagents can be used as part of the identifying system. Labeling reagents which may be used for detection include, but are not limited to, haloaromatics (e.g., perfluorobenzyl bromide), fluorescers (e.g., dansyl chloride), radioisotopes, chemiluminescers, and the like.

Depending on the chemical and physical nature of the tags, an appropriate method for separation is chosen, desirably one of various chromatographic procedures including gas chromatography (GC), liquid chromatography (LC) particularly high-performance liquid chromatography (HPLC), thin layer chromatography (TLC), electrophoresis, and the like. Instead of a chromatographic procedure, mass spectrometry can be employed for separation by mass number. Tags include: for GC: chemically inert organic molecules having the same or different molecular weights including alkanes, alkenes, arenes, halocarbons, ethers, alcohols, silanes, thioethers, and the like, particularly halogenated compounds, with or without other functionalities, for electron capture detection or mass spectroscopy detection (MS) with capillary GC separation, and for compound with elements not normally found in organic chemistry (e.g., Sn, Ge) for atom emission detection with GC capillary separation; for LC, HPLC or TLC: see above for GC, conveniently linear ethers or hydrocarbons with substitution by radioisotopes or combinations of radioisotopes for radioassay detection or suitable groups for fluorescence detection after separation; for electrophoresis: particularly functionalized charged molecules, e.g., cationic or anionic, particularly organic or inorganic acid groups, where the molecule may be further modified by having a detectable radioisotope or fluorescer for detection by electrophoresis; for mass spectroscopy: particularly different mass numbers due to different isotopes, different numbers of the same functionality or different functionalities, different members of a homologous series or combinations thereof. Alternatively, tags with mass numbers due to different isotopes can be used as internal controls for absolute quantitation.

The separation of tags from one another may involve individual techniques or combinations of techniques, e.g., chromatography and electrophoresis; gas chromatography and mass spectroscopy; and the like. The tags of the present invention will have a property which allows detection at very low levels, usually not greater than nanomole, preferably picomole or less, more preferably femtomole or less, in the presence of other compounds which may be present at significantly higher levels. For this reason, specific atomic substitutions may be used to render the labels easily detectable. Such substitutions include: (a) substitution by electronegative elements, e.g., fluorine or chlorine, for electron capture detection in conjunction with capillary GC or negative ion mass spectroscopy detection; (b) substitution by an uncommon element (excluding C, H, and O) for atomic emission detection in conjunction with capillary GC; (c) substitution by several uncommon elements for atomic emission detection to determine the ratio between the elements; (d) substitution by a radioactive element, e.g., $^3$H, for detection by autoradiography or scintillation counting in conjunction with LC, TLC or electrophoresis; (e) substitution by a multiplicity of radioactive elements having differing emissions; for detection by autoradiography or scintillation counting to determine the ratio of the different radioactive elements. In certain instances, the tags are fluorescent tags.

The mixture of tags associated with an array can be detached and subjected to an initial separation, where it is desirable to detect each of the tags separately. Once the group of tags has been separated, each of the tags may then be analyzed based on its particular functionalities and distinctive properties. Various techniques which may be used to detect the particular tags include autoradiography or scintillation counting, electron capture detection, negative or positive ion mass spectroscopy, infrared spectroscopy, ultraviolet spectroscopy, electron spin resonance spectroscopy, fluorescence, and the like.

C. Mass Spectrometers

In certain aspects, the label or tag increases the ionization efficiencies of the antigen. The mass spectrometers used in the present invention possess ionizing sources. Suitable ionizing sources include, but are not limited to, an electrospray ion source, an atmospheric pressure ionization source, and a matrix assisted laser desorption ion source. In certain aspects, the methods of the present invention use laser desorption ionization MS techniques. These techniques include, but are not limited to, MALDI, IR-MALDI, UV-MALDI, liquid-MALDI, surface-enhanced LDI (SELDI), surface enhanced neat desorption (SEND), desorption/ionization of silicon (DIOS), laser desorption/laser ionization MS, laser desorption/two-step laser ionization MS, and the like. Those of skill in the art will know of other ionization techniques as well as other mass spectrometric techniques useful in the present methods.

In other aspects, the methods of the present invention can also use electrospray ionization (ESI). In operation, mass spectrometry separates the ions according to their mass to charge ratio (m/z). Tandem mass spectrometers operate by using this separation of ions as a first fractionation step. Before entering the second mass spectrometer, ion fractions from the first are fragmented (e.g., collisionally dissociated by passage through a neutral gas, to induce fragmentation). These fragments exist as a family of subset ions of the original parent ions. Analysis of the m/z spectrum of these subset ions are used to determine the concentration level of the antigen. In certain aspects, the methods of the present invention further comprise liquid chromatography (LC) separation, such as the analytical technique, LC-tandem mass spectroscopy. In certain other aspects, single ion monitoring is the analytical technique.

IV. Applications

The systems and assays of the present invention provide methods for diagnosing particular diseases or disorders. For example, in a diagnostic kit, a collection of tagged antigens specific for a range of autoantibodies associated with one or more diseases or disorders can be arrayed and contacted with a bodily fluid containing autoantibodies whose presence or absence would indicate a particular disease or disorder. The advantage of using an array over a conventional immunoassay is the ability to include a population of antigens diagnostic for a variety of diseases or disorders on a single surface, significantly reducing time, costs, and materials needed to effect a diagnosis. In certain aspects, the present invention provides assays for the detection of diseases or the progression of diseases in a subject. For instance, the autoantibody is derived from a subject having an autoimmune disease or cancer (e.g., prostate, lung, and the like). Various autoimmune diseases are detectable using the methods and systems of the present invention. These autoimmune diseases include, but are not limited to, rheumatoid arthritis, osteoarthritis, juvenile chronic arthritis, systematic lupus erythematosus, Sjogren's syndrome, ankylosing spondylitis, psoriatic arthritis, multiple sclerosis, inflammatory bowel disease, graft-vs-host disease, and scleroderma.

It is to be appreciated that the antigens can be used to compare the protein expression profiles of cells, for example, comparisons can be made between a population of cells from one tissue, and a second tissue, or from cells derived from a particular tissue, or from different species. Comparisons can be made between normal cells and cells from the same tissue type that originate from an individual with a pathogenic disorder. For example, comparisons can be made between normal cells and cancer cells. Comparisons can additionally be made between cells in a resting state and cells in an activated state.

In other aspects, detection and characterization of bacterial or viral infection is of crucial importance in the practice of clinical microbiology and in environmental testing, such as food safety and biohazard safety testing. In another embodiment, the disclosed arrays are useful for evaluating the expression of proteins by pathogens, such as, for example, bacteria, parasites, viruses, and the like. The assays have utility as diagnostic agents as well as potential therapeutics.

In certain other aspects, the systems and assay methods herein improve diagnosis of autoimmune diseases, detect autoantibody signatures as a prognostic tool, monitor disease progression, response to therapy (e.g., epitope spreading), aid in development of antigen specific therapy, and possess utility in the discovery of novel antigens or epitopes.

V. Data Analysis

In certain other aspects, the data generated by the systems and methods provided herein is analyzed by algorithms such as pattern-recognition artificial-intelligence software for differential disease diagnosis. In some embodiments, the algorithms of the present invention comprise one or more learning statistical classifier systems. As used herein, the term "learning statistical classifier system" includes a machine learning algorithmic technique capable of adapting to complex data sets and making decisions based upon such data sets. In some embodiments, one or more learning statistical classifier systems are used, e.g., 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (CART), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the CART software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the $SVM^{light}$ software developed by Thorsten Joachims (Cornell University) or using the LIBSVM software developed by Chih-Chung Chang and Chih-Jen Lin (National Taiwan University).

The learning statistical classifier systems described herein can be trained and tested using a cohort of samples from healthy individuals, patients having an autoimmune disease, cancer patients, cancer cell lines, and the like. For example, samples from patients diagnosed by a physician, and preferably by an oncologist, as having cancer are suitable for use in training and testing the learning statistical classifier systems of the present invention. Samples from healthy individuals can include those that were not identified as having cancer. One skilled in the art will know of additional techniques and diagnostic criteria for obtaining a cohort of samples that can be used in training and testing the learning statistical classifier systems of the present invention.

VI. Examples

Example 1

Example 1 illustrates a mass tag being attached to an antigen.

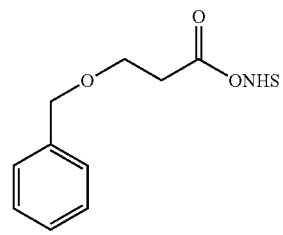

Purified GAD-65 is allowed to react with a 50-fold molar excess of benzyl oxy-propionic acid 3-sulfo-N-hydroxysuccinimide ester (1) in 50 mmol/L HEPES, 9 g/L NaCl, pH 7.4, for 4 h at room temperature. Unconjugated reagent is removed by gel filtration on a NAP-5 column (Amersham Biosciences) with 50 mmol/L HEPES, 9 g/L NaCl, 0.5 g/L sodium azide, pH 7.4, as elution buffer. The conjugated protein is stored at 4° C., either in solution or freeze-dried.

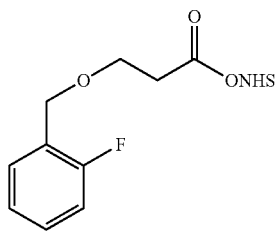

Insulin: Purified Insulin is allowed to react with a 50-fold molar excess of 2-fluoro benzyl oxy-propionic acid 3-sulfo-N-hydroxysuccinimide ester (2) in 50 mmol/L HEPES, 9 g/L NaCl, pH 7.4, for 4 h at room temperature. Unconjugated reagent is removed by gel filtration on a NAP-5 column (Amersham Biosciences) with 50 mmol/L HEPES, 9 g/L NaCl, 0.5 g/L sodium azide, pH 7.4, as elution buffer. The conjugated protein is stored at 4° C., either in solution or freeze-dried.

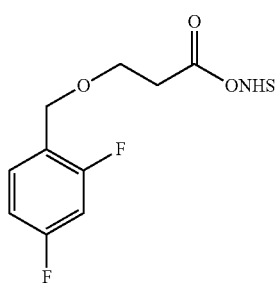

IA-2: Purified IA-2 is allowed to react with a 50-fold molar excess of 2,4-fluoro benzyl oxy-propionic acid 3-sulfo-N-hydroxysuccinimide ester (3) in 50 mmol/L HEPES, 9 g/L NaCl, pH 7.4, for 4 h at room temperature. Unconjugated reagent is removed by gel filtration on a NAP-5 column (Amersham Biosciences) with 50 mmol/L HEPES, 9 g/L NaCl, 0.5 g/L sodium azide, pH 7.4, as elution buffer. The conjugated protein is stored at 4° C., either in solution or freeze-dried.

Example 2

Example 2 illustrates a plurality of antigens being bound to an antigen support such as a polymer.

20 molar excess of purified GAD-65 is allowed to react with benzyl oxy-propionic acid amide conjugated (~1:1 conjugate), 3-sulfo-N-hydroxysuccinimide ester activated carboxy dextran (500 KD) in 50 mmol/L HEPES, 9 g/L NaCl, pH 7.4, for 4 h at room temperature. Unconjugated reagent is removed by gel filtration (Amersham Biosciences) with 50 mmol/L HEPES, 9 g/L NaCl, 0.5 g/L sodium azide, pH 7.4, as elution buffer. The conjugated dextran protein is stored at 4° C., either in solution or freeze-dried. The insulin and IA-2 conjugates were prepared in identical fashion (the mass tags were different).

20 molar excess of purified GAD-65 and an addressable oligo with a 5' thiol (50 molar excess) is allowed to react with biotin and bromoacetyl conjugated (~1:1 conjugate), 3-sulfo-N-hydroxysuccinimide ester activated carboxy dextran (500 KD) in 50 mmol/L HEPES, 9 g/L NaCl, pH 7.4, for 4 h at room temperature. Unconjugated reagent is removed by gel filtration (Amersham Biosciences) with 50 mmol/L HEPES, 9 g/L NaCl, 0.5 g/L sodium azide, pH 7.4, as elution buffer. The conjugated dextran protein is stored at 4° C., either in solution or freeze-dried.

The insulin and IA-2 conjugates were prepared in identical fashion (the addressable oligos were different). Additional conjugates that were prepared in identical fashion include: (1) ANAs; (2) negative control (GST); (3) IgG, (4) SSA/60; (5) Sm; (6) histone; (7) RF (goat IgG); (8) CENP-B; (9) CCP; (10) SSA/52; (11) U1snRNP; (12) SSB; (13) Jo-1; (14) CK19; and (15) Scl-70 (the addressable oligos were different).

Serum Calibrators

Two sets of calibrators were prepared by serial dilution of a GAD-65Ab-positive serum, insulin-Ab-positive serum, IA-2Ab-positive serum from an IDDM patient into pools of sera from healthy individuals without GAD-65, insulin, and IA-2 Abs, obtained from the Blood Bank. The calibrators were stored frozen at −70° C. Sera were pooled from three healthy individuals without GAD-65, insulin, and IA-2 Abs. Blood donors served as a negative control. The controls were stored as single-use aliquots at −70° C.

Example 3

Example 3 illustrates an assay of the present invention.

This example illustrates the assay with a specific example and detects the tag with mass spectrometry.

Serum samples (2 µL) were incubated with a mixture of mass-tag labeled IA-2, insulin and GAD-65 aliquots (40 ng) in 50 µL of 50 mmol/L Tris-HCl, 150 mmol/L NaCl, pH 7.4, containing 1 mL/L Tween 20 (TBST) overnight at 4° C. The formed immune complexes were captured by adding 5 µL of Protein A magnetic or Sepharose beads (Amersham Biosciences). Protein A magnetic beads are also available from New England Biolabs, Invitrogen Dynal AS (Dynabeads® Protein A), GenScript Corporation (Protein A MagBeads), Polysciences, Inc. (BioMag® Protein A), and Thermo Scientific Pierce Protein Research Products (MagnaBind™ Protein A Beads). After a 1 h incubation on a shaker at 4° C., the samples were transferred to a 96-well opaque filtration plate with a 0.45 µm Durapore filter at the bottom of each well (Millipore). The samples were washed 10 times with 150 µL of TBST with use of a vacuum device (Millipore). After a short drying period, the beads were transferred to a low volume 96-well plate, 10 µL of ammonium hydroxide (Aldrich) was added and incubated for 60 minutes. The released mass tags were combined with controls (deuterium labeled mass controls), and analyzed on mass spectra (PE SCIEX, API 2000; LC/MS/MS system, Perkin Elmer). All of the samples were analyzed in duplicate.

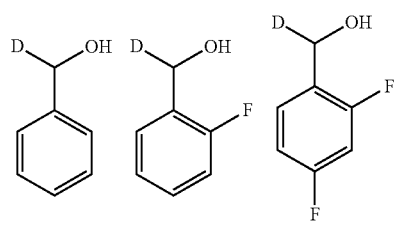

The ratio of control mass tag to specific mass tag gives one the amount of mass tag or autoantibody(s) present in the patient serum sample. The results are presented as: 100× Unknown sample (mass intensity as a ratio to control) minus negative control divided by positive control OR calibrators (mass intensity as a ratio to control) minus negative control.

Example 4

Example 4 illustrates an assay of the present invention.

Part A: Serum samples (2 µL) were incubated with a mixture of oligo-tagged dextran labeled IA-2, insulin, and GAD-65 aliquots (40 ng) in 50 µL of 50 mmol/L Tris-HCl, 150 mmol/L NaCl, pH 7.4, containing 1 mL/L Tween 20 (TBST) overnight at 4° C. The formed immune complexes were captured by adding 5 µL of protein A-2,4 DNP/anti-2,4 DNP conjugated magnetic or Sepharose beads. After a 1 h incubation on a shaker at 4° C., the samples were transferred to a 96-well opaque filtration plate with a 0.45 µm Durapore filter at the bottom of each well (Millipore). The samples were washed 3 times with 150 µL of TBST with use of a vacuum device (Millipore). After a short drying period, the beads were transferred to a low volume 96-well plate, 10 µL of 2,4 DNP (Aldrich) is added and incubated for 60 minutes. The released addressable oligo complexes were combined with controls and added to an addressable array. Wash, add Strepavidin CY5 conjugate (Molecular Probes), incubate for 30 minutes, wash, and visualize on an array reader (Perkin Elmer). All of the samples were analyzed in duplicate.

The results are presented as: 100× Unknown sample (Fluorescence intensity as a ratio to control) minus negative control divided by positive control OR calibrators (Fluorescence intensity as a ratio to control) minus negative control.

Part B: Serum samples (2 µL) were incubated with a mixture of oligo-tagged dextran labeled (1) ANAs; (2) negative control (GST); (3) IgG, (4) SSA/60; (5) Sm; (6) histone; (7) RF (goat IgG); (8) CENP-B; (9) CCP; (10) SSA/52; (11) U1snRNP; (12) SSB; (13) Jo-1; (14) CK19; or (15) Scl-70 in aliquots (40 ng) in 50 µL of 50 mmol/L Tris-HCl, 150 mmol/L NaCl, pH 7.4, containing 1 mL/L Tween 20 (TBST) overnight at 4° C. The formed immune complexes were captured by adding 5 µL of protein A-2,4 DNP/anti-2,4 DNP conjugated magnetic beads or Sepharose. After a 1 h incubation on a shaker at 4° C., the samples were transferred to a 96-well opaque filtration plate with a 0.45 µm Durapore filter at the bottom of each well (Millipore). The samples were washed 3 times with 150 µL of TBST with use of a vacuum device (Millipore). After a short drying period, the beads were transferred to a low volume 96-well plate, 10 µL of 2,4 DNP (Aldrich) is added and incubated for 60 minutes. The released addressable oligo complexes were combined with controls and added to an addressable array. Wash, add Strepavidin CY5 conjugate (Molecular Probes), incubate for 30 minutes, wash, and visualize on an array reader (Perkin Elmer). All of the samples were analyzed in duplicate.

The results are presented as: 100× unknown sample (Fluorescence intensity as a ratio to control) minus negative control divided by positive control OR calibrators (Fluorescence intensity as a ratio to control) minus negative control.

Figure 7:
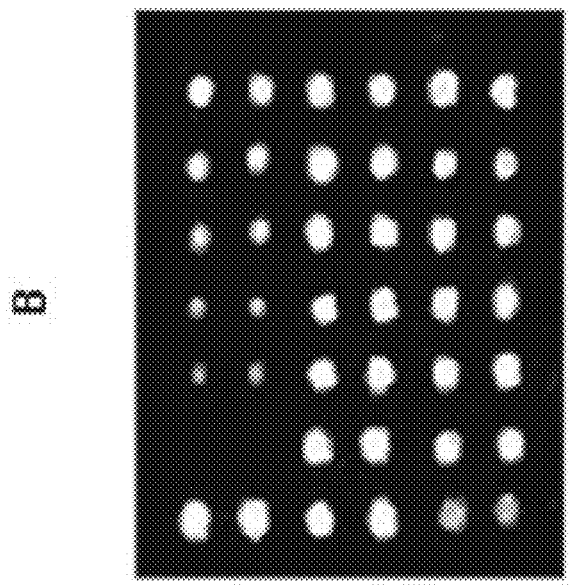
FIG. 7 illustrates an embodiment of an array of the present invention.
Figure 7:
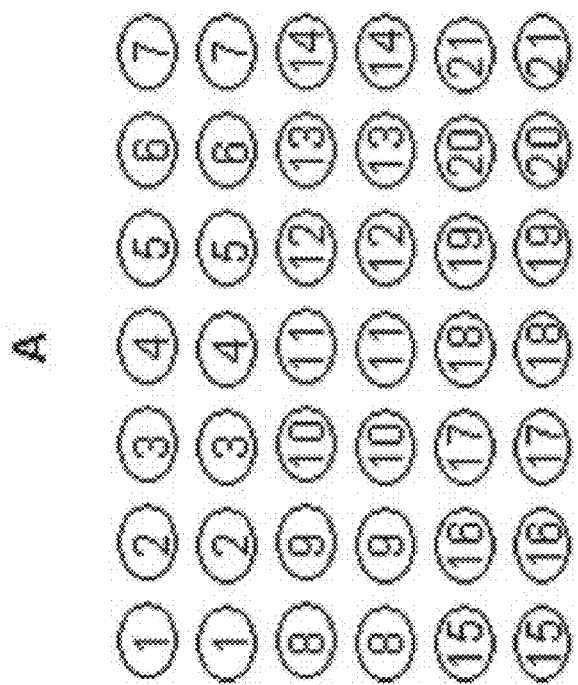

This example illustrates an autoantibody array of the present invention. As shown in FIG. 7, a schematic diagram of the array used in this study (Panel A), and a CCD-captured image of the reaction with an autoantibody-positive serum (Panel B) is illustrated.

The positions of the tagged antigens and internal controls in the array are represented in panel A as follows: 1, ANAs; 2, negative control (GST); 3, IgG (1 mg/L); 4, IgG (2 mg/L); 5, IgG (4 mg/L); 6, IgG (8 mg/L); 7, IgG (16 mg/L); 8, SSA/60; 9, Sm; 10, histone; 11, ssDNA; 12, RF (goat IgG); 13, CENP-B; 14, CCP; 15, dsDNA; 16, SSA/52; 17, U1snRNP; 18, SSB; 19, Jo-1; 20, CK19; 21, Scl-70.

Panel B shows the array after reaction with a pooled serum sample that contained autoantibodies to all of the arrayed antigens. Serum autoantibodies were detected after the array was incubated with HRP-conjugated secondary goat antibody against human IgG, followed by the addition of signal-generating substrates and signal acquisition with a CCD camera. The assay was performed in triplicate.

Example 5

Figure 8:
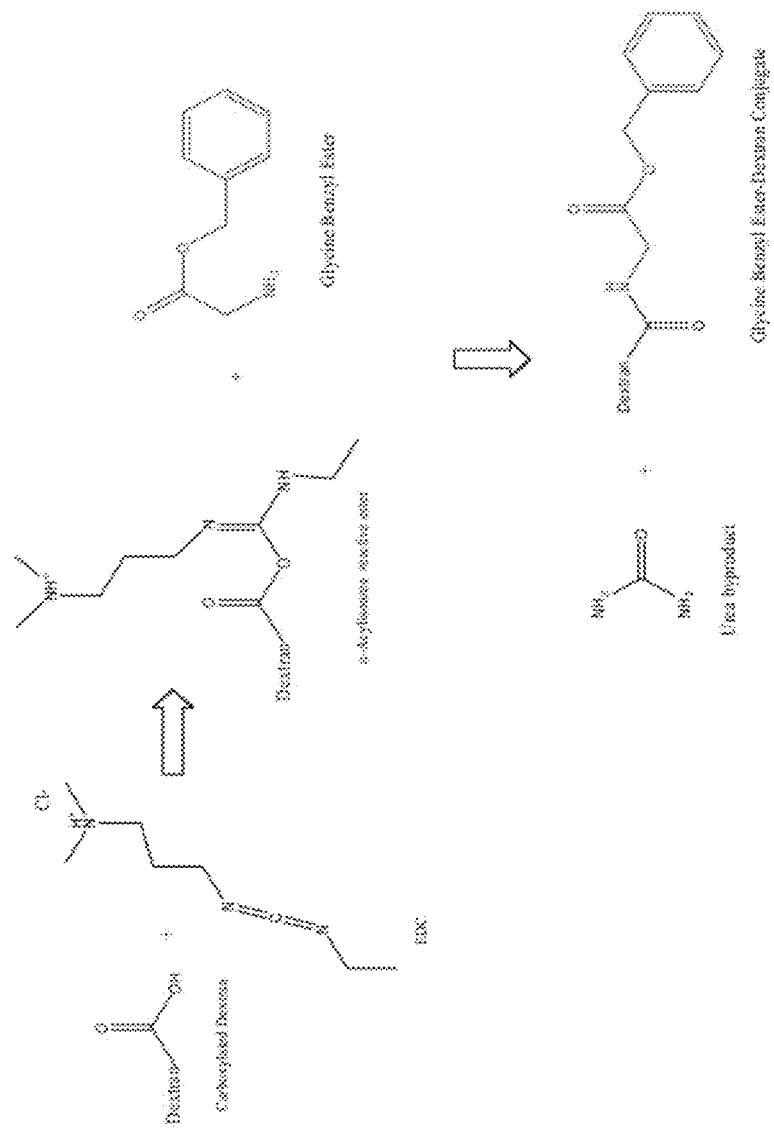
FIG. 8 illustrates one embodiment of attaching a mass tag to a support.

Example 5 illustrates coupling of glycine benzyl ester to carboxylated dextran (an antigen support) with 1-ethyl-3-(3-dimethylaminopropyl)-carbodiimide (EDC). EDC is a water-soluble derivative of carbodiimide, which forms an O-acylurea derivative (an activated ester defined in Table 1) with the carboxylated dextran. This derivative reacts readily with a glycine benzyl ester nucleophile (FIG. 8). The glycine benzyl ester forms a glycine benzyl ester-dextran conjugate, wherein the benzyl ester can be hydrolyzed to release the mass tag. Benzyl alcohol is the detected species.

In this example, 10 mg of 500 kD carboxylated dextran (an antigen support) was dissolved in 460 µL of 50 mM MES pH 4.5. Thereafter, 1.4-1.7 mg of EDC was added and stirred for 30 min at 4° C. Next, 40.3 µL of 100 mg/mL glycine benzyl ester was added and stirred 1 hour at 4° C. Thereafter, the pH is adjusted to 7.5 and stirred at room temperature for 1 hour. To hydrolyze the ester bond and remove the mass tag, the conjugate was treated with 0.1M ammonium hydroxide and incubated in a 65° C. water bath for 1 to 2.5 hours. As controls, dextran, buffer, and glycine benzyl ester were also treated with 0.1M ammonium hydroxide and incubated in a 65° C. water bath for 2.5 hours as controls.

Example 6

Figure 9:
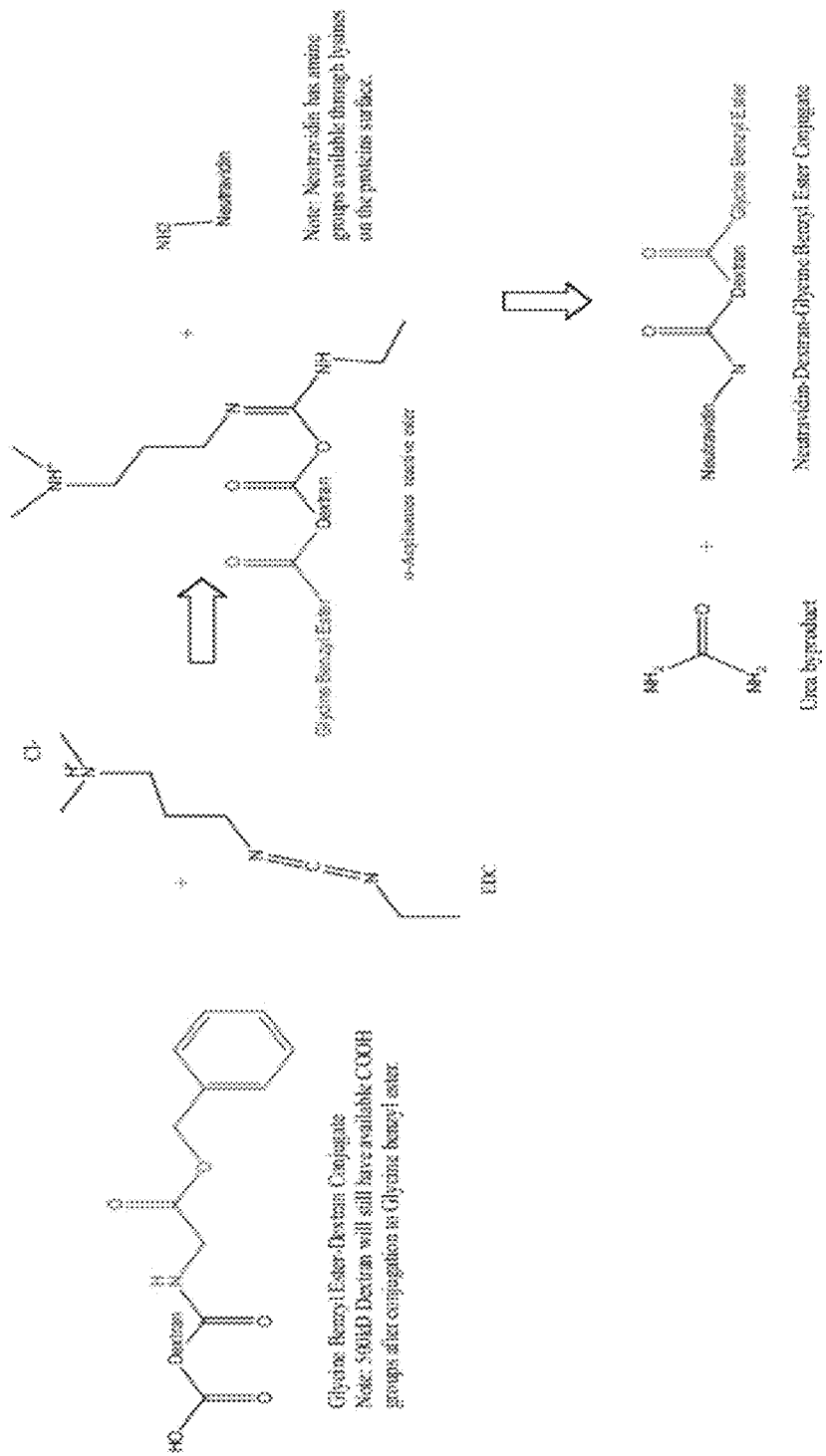
FIG. 9 illustrates an embodiment of an attached mass tag to a support with a "quick-attach" antigen linker.
Figure 10:
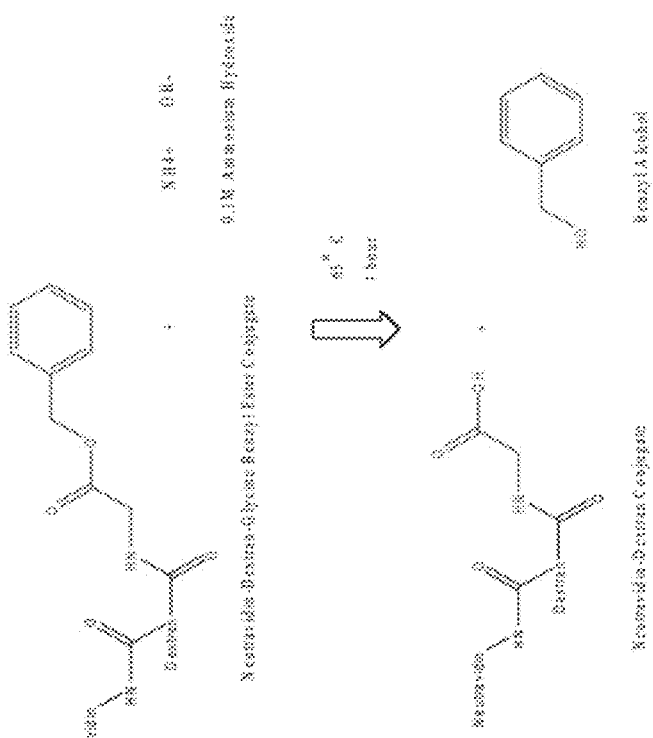
FIG. 10 illustrates an embodiment of release of an attached mass tag from a support with a "quick-attach" antigen linker.

Example 6 illustrates a method for addition of neutravidin to an antigen support of dextran coupled with glycine benzyl ester. This allows for a "quick attach" plurality of antigens. As shown in the reaction of FIG. 9, 3 mg of a lyophilized 1000:1 conjugate (benzyl ester to dextran) from Example 5 is dissolved in 200 µL of 50 mM MES at pH 4.5. Next, 0.7 mg of EDC is added and stirred for 30 min at 4° C. Afterwards, 1.8 mg of neutravidin is added and stirred 1 hour at 4° C. The reaction had a final concentration of dextran of 30 µM and neutravidin of 150 µM. Thereafter, the pH is adjusted to 7.5 and stirred at room temperature for 1 hour. The addition of 5.5 µL of 4N NaOH to the reaction yields a neutravidin dextran-glycine benzyl ester conjugate. The conjugate is then dialyzed against PBS using 100,000 MWCO dialysis tube. Afterwards, the final volume is calculated and stored at −20° C. Similar to Example 5, FIG. 10 shows that the ester bond is hydrolyzed to remove the mass tag. The conjugate was treated with 0.1M ammonium hydroxide and incubated in a 65° C. water bath for 1 to 2.5 hours. As controls, dextran, buffer, and glycine benzyl ester were treated with 0.1M ammonium hydroxide and incubated in a 65° C. water bath for 2.5 hours. The HPLC with a C18 column can resolve the dextran, the conjugate, the glycine bezyl ester and the treated conjugate. Various antigens having biotin attached as the second binding member can be attached using the "quick-attach" system.

Example 7

Figure 11:
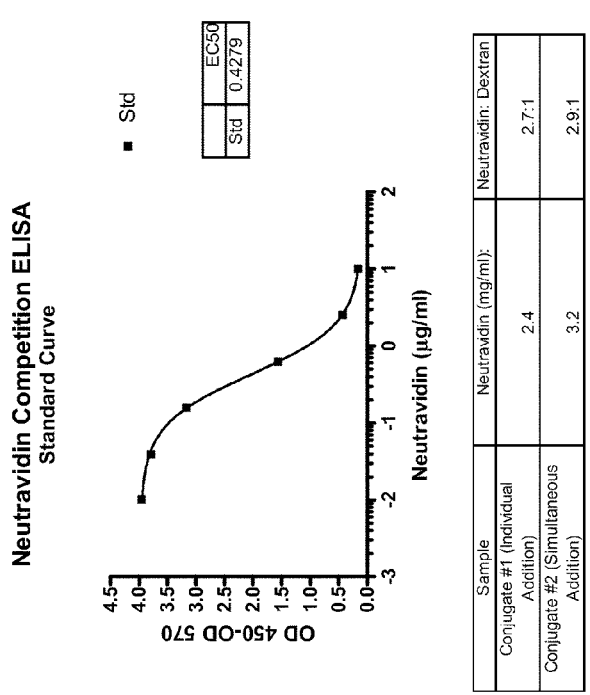
FIG. 11 illustrates an embodiment of a competitive ELISA using a conjugate of the present invention.

Example 7 illustrates a competitive ELISA to detect neutravidin conjugation. A standard curve was prepared in a competitive ELISA format using a neutravidin-biotin binding assay. Free neutravidin or neutravidin conjugates compete with neutravidin coated on the ELISA plate to bind biotin-HRP. As shown in FIG. 11, the boxed results indicate that the neutravidin-dextran conjugates also compete in the ELISA with neutravidin bound to the plate.

All publications, patents and patent publications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An assay method for detecting an autoantibody in a sample from a subject, said method comprising:
    (a) contacting a tagged antigen with a sample having an autoantibody specific for said tagged antigen to transform said autoantibody into an immunological pair, wherein said tagged antigen is a plurality of antigens on a support;
    (b) contacting said immunological pair with a solid support having a binding member specific for said immunological pair to transform said immunological pair into a protein complex;
    (c) separating said protein complex from said sample to form an isolated protein complex; and
    (d) releasing said tag from said isolated protein complex for detection.

2. The assay method of claim 1, wherein said tag is detected by mass spectrometry.

3. The assay method of claim 1, wherein said binding member is selected from the group consisting of an antigen, an antibody, biotin, avidin, streptavidin, anti-biotin; folate, folate-binding protein, IgG, Protein A, Protein G, a carbohydrate, lectin, and a nucleic acid.

4. The assay method of claim 1, wherein said binding member is a protein which binds to said immunological pair.

5. The assay method of claim 1, wherein the solid support is selected from the group consisting of polystyrene, cellulose, nitrocellulose, a glass bead, and a magnetic bead.

6. The assay method of claim 5, wherein the solid support is a magnetic bead.

7. The assay method of claim 1, wherein said sample is a member selected from the group consisting of whole blood, serum, plasma, urine, seminal fluid, and saliva.

8. The assay method of claim 7, wherein said sample is whole blood.

9. The assay method of claim 1, wherein said autoantibody is derived from a subject having an autoimmune disease selected from the group consisting of rheumatoid arthritis, osteoarthritis, juvenile chronic arthritis, systematic lupus erythematosus, Sjogren's syndrome, ankylosing spondylitis, psoriatic arthritis, multiple sclerosis, inflammatory bowel disease, graft-vs-host disease, and scleroderma.

10. The assay method of claim 1, wherein said support is a hydrophilic molecule.

11. The assay method of claim 10, wherein said hydrophilic molecule is a polymer.

12. The assay method of claim 11, wherein said polymer is a member selected from the group consisting of polyethylene glycol, dextran, dextran carboxylic acid polyvinyl pyrrolidone, sugar alcohols, polyoxyethylene polyoxypropylene glycol, and a mixture thereof.

13. The assay method of claim 11, wherein said plurality of antigens is attached to said polymer in a "quick-attach" system.

14. The assay method of claim 1, wherein said autoantibody is a plurality of autoantibodies.

15. The assay method of claim 14, wherein said plurality of antigens is specific for said plurality of autoantibodies which form a plurality of immunological pairs.

16. The assay method of claim 15, wherein the increase in affinity from the formation of said plurality of immunological pairs allows for increased detection of a single immunological pair.

17. The assay method of claim 1, wherein said tagged antigen further comprises a first binding member having affinity to an addressable support comprising a second binding member.

18. The assay method of claim 17, wherein said first binding member forms a bound pair with said second binding member on said addressable support.

19. A method for diagnosing a disease or disorder in a subject, said method comprising:
    (a) contacting a tagged antigen with a sample from said subject having an autoantibody specific for said tagged antigen to transform said tagged antigen into an immunological pair, wherein said tagged antigen is a plurality of antigens on a support;
    (b) contacting said immunological pair with a solid support having a binding member specific for said immunological pair to transform said immunological pair into a protein complex;
    (c) separating said protein complex from said sample to form an isolated protein complex;
    (d) releasing said tag from said isolated protein complex for detection; and
    (e) detecting the amount of said tag, wherein the amount of said tag is indicative of the amount of said autoantibody, and wherein said disease or disorder is determined to be present when the amount of said autoantibody differs from a control value representing the amount of said autoantibody in a sample from a subject not having said disease or disorder.

* * * * *